US011049134B2

(12) United States Patent
Pradeep et al.

(10) Patent No.: US 11,049,134 B2
(45) **Date of Patent: *Jun. 29, 2021**

(54) NEURO-PHYSIOLOGY AND NEURO-BEHAVIORAL BASED STIMULUS TARGETING SYSTEM

(71) Applicant: Nielsen Consumer LLC, New York, NY (US)

(72) Inventors: A. K. Pradeep, Berkeley, CA (US); Robert T. Knight, Berkeley, CA (US); Ramachandran Gurumoorthy, Berkeley, CA (US)

(73) Assignee: Nielsen Consumer LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/790,160

(22) Filed: Feb. 13, 2020

(65) Prior Publication Data

US 2020/0234329 A1 Jul. 23, 2020

Related U.S. Application Data

(63) Continuation of application No. 15/989,987, filed on May 25, 2018, now Pat. No. 10,580,031, which is a (Continued)

(51) Int. Cl.

*G06Q 30/00* (2012.01)
*G06Q 30/02* (2012.01)

(Continued)

(52) U.S. Cl.

CPC ....... *G06Q 30/0244* (2013.01); *A61B 5/4017* (2013.01); *G06Q 10/0637* (2013.01);

(Continued)

(58) Field of Classification Search

CPC ...... G06Q 20/12; G06Q 20/123; G06Q 30/00; G06Q 30/0641

See application file for complete search history.

(56) References Cited

U.S. PATENT DOCUMENTS

| | | | |
|---|---|---|---|
| 2,549,836 | A | 4/1951 | McIntyre et al. |
| 3,490,439 | A | 1/1970 | Rolston |

(Continued)

FOREIGN PATENT DOCUMENTS

| | | |
|---|---|---|
| EP | 1087618 | 3/2001 |
| EP | 1609418 | 12/2005 |

(Continued)

OTHER PUBLICATIONS

Final Rejection, issued by the United States Patent and Trademark Office in connection with U.S. Appl. No. 12/056,211, dated Jul. 8, 2011, 16 pages.

(Continued)

*Primary Examiner* — Scott S Trotter
(74) *Attorney, Agent, or Firm* — Hanley, Flight & Zimmerman, LLC

(57) ABSTRACT

An example system includes an analyzer to determine a first distance between (1) a first peak in a first frequency band of first neuro-response data gathered from a subject while exposed to media and (2) a second peak in the first frequency band; determine a second distance between (1) a third peak in the first frequency band and either (2) the second peak in the first frequency band or (3) a fourth peak in the first frequency band and determine a first difference between the first distance and the second distance. The example system includes a selector to determine a modification for the media based on the first difference and a modifier to implement the modification for presentation of the media.

20 Claims, 7 Drawing Sheets

Related U.S. Application Data continuation of application No. 13/730,550, filed on Dec. 28, 2012, now abandoned, which is a continuation of application No. 12/122,262, filed on May 16, 2008, now Pat. No. 8,392,253.

(60) Provisional application No. 60/938,286, filed on May 16, 2007.

(51) Int. Cl.

| | |
|---|---|
| ***G06Q 10/06*** | (2012.01) |
| ***A61B 5/00*** | (2006.01) |
| ***G16H 10/20*** | (2018.01) |
| *A61B 5/16* | (2006.01) |
| *A61B 5/0533* | (2021.01) |
| *A61B 5/1171* | (2016.01) |
| *A61B 5/318* | (2021.01) |
| *A61B 5/369* | (2021.01) |
| *A61B 5/398* | (2021.01) |

(52) U.S. Cl.

CPC ..... *G06Q 30/0242* (2013.01); *G06Q 30/0269* (2013.01); *G06Q 30/0271* (2013.01); *G16H 10/20* (2018.01); *A61B 5/0533* (2013.01); *A61B 5/1176* (2013.01); *A61B 5/163* (2017.08); *A61B 5/318* (2021.01); *A61B 5/369* (2021.01); *A61B 5/398* (2021.01); *A61B 5/4035* (2013.01)

(56) References Cited

U.S. PATENT DOCUMENTS

| | | | | |
|---|---|---|---|---|
| 3,572,322 | A | 3/1971 | Wade | |
| 3,735,753 | A | 5/1973 | Pisarski | |
| 3,880,144 | A | 4/1975 | Coursin et al. | |
| 3,901,215 | A | 8/1975 | John | |
| 3,998,213 | A | 12/1976 | Price | |
| 4,075,657 | A | 2/1978 | Weinblatt | |
| 4,145,122 | A | 3/1979 | Rinard et al. | |
| 4,149,716 | A | 4/1979 | Scudder | |
| 4,201,224 | A | 5/1980 | John | |
| 4,279,258 | A | 7/1981 | John | |
| 4,411,273 | A | 10/1983 | John | |
| 4,417,592 | A | 11/1983 | John | |
| 4,537,198 | A | 8/1985 | Corbett | |
| 4,557,270 | A | 12/1985 | John | |
| 4,610,259 | A | 9/1986 | Cohen et al. | |
| 4,613,951 | A | 9/1986 | Chu | |
| 4,626,904 | A | 12/1986 | Lurie | |
| 4,632,122 | A | 12/1986 | Johansson et al. | |
| 4,683,892 | A | 8/1987 | Johansson et al. | |
| 4,686,999 | A | 8/1987 | Snyder et al. | |
| 4,695,879 | A | 9/1987 | Weinblatt | |
| 4,736,751 | A | 4/1988 | Gevins et al. | |
| 4,800,888 | A | 1/1989 | Itil et al. | |
| 4,802,484 | A | 2/1989 | Friedman et al. | |
| 4,846,190 | A | 7/1989 | John | |
| 4,859,050 | A | 8/1989 | Borah et al. | |
| 4,870,579 | A | 9/1989 | Hey | |
| 4,885,687 | A | 12/1989 | Carey | |
| 4,894,777 | A | 1/1990 | Negishi et al. | |
| 4,913,160 | A | 4/1990 | John | |
| 4,967,038 | A | 10/1990 | Gevins et al. | |
| 4,955,388 | A | 11/1990 | Silberstein | |
| 4,973,149 | A | 11/1990 | Hutchinson | |
| 4,987,903 | A | 1/1991 | Keppel et al. | |
| 5,003,986 | A | 4/1991 | Finitzo et al. | |
| 5,010,891 | A | 4/1991 | Chamoun | |
| 5,038,782 | A | 8/1991 | Gevins et al. | |
| 5,052,401 | A | 10/1991 | Sherwin | |
| 5,083,571 | A | 1/1992 | Prichep | |
| RE34,015 | E | 8/1992 | Duffy | |
| 5,137,027 | A | 8/1992 | Rosenfeld | |
| 5,213,338 | A | 5/1993 | Brotz | |
| 5,226,177 | A | 7/1993 | Nickerson | |
| 5,243,517 | A * | 9/1993 | Schmidt | A61B 5/0484 600/544 |
| 5,273,037 | A | 12/1993 | Itil et al. | |
| 5,291,888 | A | 3/1994 | Tucker | |
| 5,293,867 | A | 3/1994 | Oommen | |
| 5,295,491 | A | 3/1994 | Gevins | |
| 5,331,544 | A | 7/1994 | Lu et al. | |
| 5,339,826 | A | 8/1994 | Schmidt et al. | |
| 5,345,281 | A | 9/1994 | Taboada et al. | |
| 5,357,957 | A | 10/1994 | Itil et al. | |
| 5,363,858 | A | 11/1994 | Farwell | |
| 5,392,788 | A | 2/1995 | Hudspeth | |
| 5,406,956 | A | 4/1995 | Farwell | |
| 5,410,609 | A | 4/1995 | Kado et al. | |
| 5,436,830 | A | 7/1995 | Zaltman | |
| 5,447,166 | A | 9/1995 | Gevins | |
| 5,450,855 | A | 9/1995 | Rosenfeld | |
| 5,474,082 | A | 12/1995 | Junker | |
| 5,479,934 | A | 1/1996 | Imran | |
| 5,513,649 | A | 5/1996 | Gevins et al. | |
| 5,518,007 | A | 5/1996 | Becker | |
| 5,537,618 | A | 7/1996 | Boulton et al. | |
| 5,550,928 | A | 8/1996 | Lu et al. | |
| 5,617,855 | A | 4/1997 | Waletzky et al. | |
| 5,655,534 | A | 8/1997 | Ilmoniemi | |
| 5,676,138 | A | 10/1997 | Zawilinski | |
| 5,676,148 | A | 10/1997 | Koo et al. | |
| 5,687,322 | A | 11/1997 | Deaton et al. | |
| 5,720,619 | A | 2/1998 | Fisslinger | |
| 5,724,987 | A | 3/1998 | Gevins et al. | |
| 5,726,701 | A | 3/1998 | Needham | |
| 5,729,205 | A | 3/1998 | Kwon | |
| 5,736,986 | A | 4/1998 | Sever, Jr. | |
| 5,740,035 | A | 4/1998 | Cohen et al. | |
| 5,762,611 | A | 6/1998 | Lewis et al. | |
| 5,771,897 | A | 6/1998 | Zufrin | |
| 5,774,591 | A | 6/1998 | Black et al. | |
| 5,787,187 | A | 7/1998 | Bouchard et al. | |
| 5,800,351 | A | 9/1998 | Mann | |
| 5,802,208 | A | 9/1998 | Podilchuk et al. | |
| 5,802,220 | A | 9/1998 | Black et al. | |
| 5,812,642 | A | 9/1998 | Leroy | |
| 5,817,029 | A | 10/1998 | Gevins et al. | |
| 5,842,199 | A | 11/1998 | Miller et al. | |
| 5,848,399 | A | 12/1998 | Burke | |
| 5,892,566 | A | 4/1999 | Bullwinkel | |
| 5,945,863 | A | 8/1999 | Coy | |
| 5,961,332 | A | 10/1999 | Joao | |
| 5,974,262 | A | 10/1999 | Fuller et al. | |
| 5,983,129 | A | 11/1999 | Cowan et al. | |
| 5,995,868 | A | 11/1999 | Dorfmeister et al. | |
| 6,001,065 | A | 12/1999 | DeVito | |
| 6,016,475 | A | 1/2000 | Miller et al. | |
| 6,021,346 | A | 2/2000 | Ryu et al. | |
| 6,032,129 | A | 2/2000 | Greef et al. | |
| 6,052,619 | A | 4/2000 | John | |
| 6,088,040 | A | 7/2000 | Oda et al. | |
| 6,099,319 | A | 8/2000 | Zaltman et al. | |
| 6,120,440 | A | 9/2000 | Goknar | |
| 6,128,521 | A | 10/2000 | Marro et al. | |
| 6,154,669 | A | 11/2000 | Hunter et al. | |
| 6,155,927 | A | 12/2000 | Levasseur et al. | |
| 6,161,030 | A | 12/2000 | Levendowski et al. | |
| 6,170,018 | B1 | 1/2001 | Voll et al. | |
| 6,171,239 | B1 | 1/2001 | Humphrey | |
| 6,173,260 | B1 | 1/2001 | Slaney | |
| 6,175,753 | B1 | 1/2001 | Menkes et al. | |
| 6,182,113 | B1 | 1/2001 | Narayanaswami | |
| 6,190,314 | B1 | 2/2001 | Ark et al. | |
| 6,212,502 | B1 | 4/2001 | Ball et al. | |
| 6,228,038 | B1 | 5/2001 | Claessens | |
| 6,236,885 | B1 | 5/2001 | Hunter et al. | |
| 6,236,975 | B1 | 5/2001 | Boe et al. | |
| 6,254,536 | B1 | 7/2001 | DeVito | |
| 6,280,198 | B1 | 8/2001 | Calhoun et al. | |
| 6,286,005 | B1 | 9/2001 | Cannon | |
| 6,289,234 | B1 | 9/2001 | Mueller | |

(56) References Cited

U.S. PATENT DOCUMENTS 6,292,688 B1 9/2001 Patton
6,299,308 B1 10/2001 Voronka et al.
6,301,492 B1 10/2001 Zonenshayn
6,301,493 B1 10/2001 Marro et al.
6,315,569 B1 11/2001 Zaltman
6,330,470 B1 12/2001 Tucker et al.
6,334,778 B1 1/2002 Brown
6,358,201 B1 3/2002 Childre et al.
6,370,513 B1 4/2002 Kolawa et al.
6,374,143 B1 4/2002 Berrang et al.
6,381,481 B1 4/2002 Levendowski et al.
6,398,643 B1 6/2002 Knowles et al.
6,422,999 B1 7/2002 Hill
6,434,419 B1 8/2002 Gevins et al.
6,435,878 B1 8/2002 Reynolds et al.
6,453,194 B1 9/2002 Hill
6,453,241 B1 9/2002 Bassett, Jr. et al.
6,487,444 B2 11/2002 Mimura
6,488,617 B1 12/2002 Katz
6,510,333 B1 1/2003 Licata et al.
6,510,340 B1 1/2003 Jordan
6,520,905 B1 2/2003 Surve et al.
6,545,685 B1 4/2003 Dorbie
6,575,902 B1 6/2003 Burton
6,577,329 B1 6/2003 Flickner et al.
6,585,521 B1 7/2003 Obrador
6,594,521 B2 7/2003 Tucker
6,598,006 B1 7/2003 Honda et al.
6,609,024 B1 8/2003 Ryu et al.
6,648,822 B2 11/2003 Hamamoto et al.
6,652,283 B1 11/2003 Van Schaack et al.
6,654,626 B2 11/2003 Devlin et al.
6,662,052 B1 12/2003 Sarwal et al.
6,665,560 B2 12/2003 Becker et al.
6,678,685 B2 1/2004 McGill et al.
6,688,890 B2 2/2004 von Buegner
6,708,051 B1 3/2004 Durousseau
6,712,468 B1 3/2004 Edwards
6,754,524 B2 6/2004 Johnson, Jr.
6,757,556 B2 6/2004 Gopenathan et al.
6,788,882 B1 9/2004 Geer et al.
6,792,304 B1 9/2004 Silberstein
6,842,877 B2 1/2005 Robarts et al.
6,850,252 B1 2/2005 Hoffberg
6,852,875 B2 2/2005 Prakash
6,888,457 B2 5/2005 Wilkinson et al.
6,904,408 B1 6/2005 McCarthy et al.
6,950,698 B2 9/2005 Sarkela et al.
6,958,710 B2 10/2005 Zhang et al.
6,973,342 B1 12/2005 Swanson
6,993,380 B1 1/2006 Modarres
7,020,508 B2 3/2006 Stivoric et al.
7,043,056 B2 5/2006 Edwards et al.
7,047,550 B1 5/2006 Yasukawa et al.
7,113,916 B1 9/2006 Hill
7,120,880 B1 10/2006 Dryer et al.
7,130,673 B2 10/2006 Tolvanen-Laakso et al.
7,150,715 B2 12/2006 Collura et al.
7,164,967 B2 1/2007 Etienne-Cummings et al.
7,177,675 B2 2/2007 Suffin et al.
7,222,071 B2 5/2007 Neuhauser et al.
7,246,081 B2 7/2007 Hill
7,249,708 B2 7/2007 McConnell et al.
7,272,982 B2 9/2007 Neuhauser et al.
7,286,871 B2 10/2007 Cohen
7,340,060 B2 3/2008 Tomkins et al.
7,359,894 B1 4/2008 Liebman et al.
7,391,835 B1 6/2008 Gross et al.
7,394,385 B2 7/2008 Franco, Jr. et al.
7,408,460 B2 8/2008 Crystal et al.
7,420,464 B2 9/2008 Fitzgerald et al.
7,443,292 B2 10/2008 Jensen et al.
7,460,827 B2 12/2008 Schuster et al.
7,463,143 B2 12/2008 Forr et al.
7,463,144 B2 12/2008 Crystal et al.
7,471,987 B2 12/2008 Crystal et al.
7,483,835 B2 1/2009 Neuhauser et al.
7,483,844 B2 1/2009 Takakura et al.
7,496,400 B2 2/2009 Hoskonen et al.
7,548,774 B2 6/2009 Kurtz et al.
7,551,952 B2 6/2009 Gevins et al.
7,592,908 B2 9/2009 Zhang et al.
7,614,066 B2 11/2009 Urdang et al.
7,623,823 B2 11/2009 Zito et al.
7,630,757 B2 12/2009 Dorfmeister et al.
7,636,456 B2 12/2009 Collins et al.
7,641,341 B2 1/2010 Weinblatt
7,650,793 B2 1/2010 Jensen et al.
7,658,327 B2 2/2010 Tuchman et al.
7,689,272 B2 3/2010 Farwell
7,697,979 B2 4/2010 Martinerie et al.
7,698,238 B2 4/2010 Barletta et al.
7,720,351 B2 5/2010 Levitan
7,729,755 B2 6/2010 Laken
7,765,564 B2 7/2010 Deng
7,774,052 B2 8/2010 Burton et al.
7,797,186 B2 9/2010 Dybus
7,809,420 B2 10/2010 Hannula et al.
7,840,248 B2 11/2010 Fuchs et al.
7,840,250 B2 11/2010 Tucker
7,844,484 B2 11/2010 Arnett et al.
7,865,394 B1 1/2011 Calloway et al.
7,892,764 B2 2/2011 Xiong et al.
7,895,075 B2 2/2011 Gettys et al.
7,895,625 B1 2/2011 Bryan et al.
7,908,133 B2 3/2011 Neuhauser
7,917,366 B1 3/2011 Levanon et al.
7,930,199 B1 4/2011 Hill
7,962,315 B2 6/2011 Jensen et al.
7,988,557 B2 8/2011 Soderland
8,014,847 B2 * 9/2011 Shastri .................. A61B 5/055
600/410
8,055,722 B2 11/2011 Hille
8,069,125 B2 11/2011 Jung et al.
8,073,707 B2 12/2011 Teller et al.
8,082,215 B2 12/2011 Jung et al.
8,086,563 B2 12/2011 Jung et al.
8,098,152 B2 1/2012 Zhang et al.
8,103,328 B2 1/2012 Turner et al.
8,126,220 B2 2/2012 Greig
8,135,606 B2 3/2012 Dupree
8,151,298 B2 4/2012 Begeja et al.
8,165,916 B2 4/2012 Hoffberg et al.
8,196,168 B1 6/2012 Bryan et al.
8,200,775 B2 6/2012 Moore
8,209,224 B2 6/2012 Pradeep et al.
8,229,469 B2 7/2012 Zhang et al.
8,235,725 B1 8/2012 Hill
8,270,814 B2 9/2012 Pradeep et al.
8,296,172 B2 10/2012 Marci et al.
8,300,526 B2 10/2012 Saito et al.
8,335,715 B2 12/2012 Pradeep et al.
8,381,244 B2 2/2013 King et al.
8,386,312 B2 2/2013 Pradeep et al.
8,386,313 B2 2/2013 Pradeep et al.
8,392,250 B2 3/2013 Pradeep et al.
8,392,251 B2 3/2013 Pradeep et al.
8,392,253 B2 3/2013 Pradeep et al.
8,392,254 B2 3/2013 Pradeep et al.
8,392,255 B2 3/2013 Pradeep et al.
8,396,744 B2 3/2013 Pradeep et al.
8,473,345 B2 6/2013 Pradeep et al.
8,484,081 B2 7/2013 Pradeep et al.
8,484,801 B2 7/2013 Pradeep et al.
8,494,610 B2 7/2013 Pradeep et al.
8,494,905 B2 7/2013 Pradeep et al.
8,533,042 B2 9/2013 Pradeep et al.
8,548,852 B2 10/2013 Pradeep et al.
8,561,095 B2 10/2013 Dimitrova et al.
8,635,105 B2 1/2014 Pradeep et al.
8,655,428 B2 2/2014 Pradeep et al.
8,655,437 B2 2/2014 Pradeep et al.
8,709,054 B2 4/2014 Lowry et al.
8,762,202 B2 6/2014 Pradeep et al.

(56) References Cited

U.S. PATENT DOCUMENTS 8,764,652 B2 7/2014 Lee et al.
8,788,372 B2 7/2014 Kettner et al.
8,793,715 B1 7/2014 Weitzenfeld et al.
9,336,535 B2 5/2016 Pradeep et al.
9,560,984 B2 2/2017 Pradeep et al.
9,886,981 B2 2/2018 Pradeep et al.
10,068,248 B2 9/2018 Knight et al.
10,127,572 B2 11/2018 Pradeep et al.
10,140,628 B2 11/2018 Pradeep et al.
10,198,713 B2 2/2019 Marci et al.
10,269,036 B2 4/2019 Knight et al.
10,580,031 B2 3/2020 Pradeep et al.
10,679,241 B2 6/2020 Pradeep et al.
10,733,625 B2 8/2020 Pradeep et al.
10,937,051 B2 3/2021 Pradeep et al.
2001/0013009 A1 8/2001 Greening et al.
2001/0020236 A1 9/2001 Cannon
2001/0029468 A1 10/2001 Yamaguchi et al.
2001/0032140 A1 10/2001 Hoffman
2001/0056225 A1 12/2001 DeVito
2002/0053076 A1 5/2002 Landesmann
2002/0055857 A1 5/2002 Mault
2002/0056087 A1 5/2002 Berezowski et al.
2002/0056124 A1 5/2002 Hay
2002/0059577 A1 5/2002 Lu et al.
2002/0065826 A1 5/2002 Bell et al.
2002/0072952 A1 6/2002 Hamzy et al.
2002/0077534 A1 6/2002 DuRousseau
2002/0082902 A1 6/2002 Ando et al.
2002/0103429 A1 8/2002 deCharms
2002/0111796 A1 8/2002 Nemoto
2002/0116042 A1 8/2002 Boling
2002/0143627 A1 10/2002 Barsade et al.
2002/0155878 A1 10/2002 Lert, Jr. et al.
2002/0156842 A1 10/2002 Signes et al.
2002/0169665 A1 11/2002 Hughes et al.
2002/0178440 A1 11/2002 Agnihotri
2002/0188216 A1 12/2002 Kayyali et al.
2002/0188217 A1 12/2002 Farwell
2002/0193670 A1 12/2002 Garfield et al.
2003/0013981 A1 1/2003 Gevins et al.
2003/0036955 A1 2/2003 Tanaka et al.
2003/0037333 A1 2/2003 Ghashghai et al.
2003/0044021 A1 3/2003 Wilkinson et al.
2003/0044050 A1 3/2003 Clark et al.
2003/0059750 A1 3/2003 Bindler et al.
2003/0063222 A1 4/2003 Creed et al.
2003/0065524 A1 4/2003 Giacchetti et al.
2003/0073921 A1 4/2003 Sohmer et al.
2003/0081834 A1 5/2003 Philomin et al.
2003/0093792 A1 5/2003 Labeeb et al.
2003/0100998 A2 5/2003 Brunner et al.
2003/0104865 A1 6/2003 Itkis et al.
2003/0118975 A1 6/2003 Stamm et al.
2003/0131351 A1 7/2003 Shapira
2003/0149344 A1 8/2003 Nizan
2003/0165270 A1 9/2003 Endrikhovski et al.
2003/0177488 A1 9/2003 Smith et al.
2003/0204412 A1 10/2003 Brier
2003/0208754 A1 11/2003 Sridhar et al.
2003/0233278 A1 12/2003 Marshall
2004/0001616 A1 1/2004 Gutta et al.
2004/0005143 A1 1/2004 Tsuru et al.
2004/0013398 A1 1/2004 Miura et al.
2004/0015608 A1 1/2004 Ellis et al.
2004/0055448 A1 3/2004 Byon
2004/0068431 A1 4/2004 Smith et al.
2004/0073129 A1 4/2004 Caldwell et al.
2004/0088289 A1 5/2004 Xu et al.
2004/0092809 A1 5/2004 DeCharms
2004/0098298 A1 5/2004 Yin
2004/0101212 A1 5/2004 Fedorovskaya et al.
2004/0133081 A1 7/2004 Teller et al.
2004/0187167 A1 9/2004 Maguire et al.
2004/0193068 A1 9/2004 Burton et al.
2004/0210159 A1* 10/2004 Kibar .................. A61B 5/4803 600/558
2004/0219184 A1 11/2004 Brown et al.
2004/0220483 A1 11/2004 Yeo et al.
2004/0236623 A1 11/2004 Gopalakrishnan
2005/0010475 A1 1/2005 Perkowski et al.
2005/0041951 A1 2/2005 Inoue et al.
2005/0043646 A1 2/2005 Viirre et al.
2005/0060312 A1 3/2005 Curtiss et al.
2005/0062637 A1 3/2005 El Zabadani et al.
2005/0071462 A1 3/2005 Bodin et al.
2005/0071865 A1 3/2005 Martins
2005/0076359 A1 4/2005 Pierson et al.
2005/0079474 A1 4/2005 Lowe
2005/0097594 A1 5/2005 O'Donnell et al.
2005/0107716 A1 5/2005 Eaton et al.
2005/0108092 A1 5/2005 Campbell et al.
2005/0113649 A1 5/2005 Bergantino
2005/0132401 A1 6/2005 Boccon-Gibod et al.
2005/0143629 A1 6/2005 Farwell
2005/0149964 A1 7/2005 Thomas et al.
2005/0154290 A1 7/2005 Langleben
2005/0165766 A1 7/2005 Szabo
2005/0177058 A1 8/2005 Sobell
2005/0197590 A1 9/2005 Osorio et al.
2005/0203798 A1 9/2005 Jensen et al.
2005/0216071 A1 9/2005 Devlin et al.
2005/0216243 A1 9/2005 Graham et al.
2005/0223237 A1 10/2005 Barletta et al.
2005/0227233 A1 10/2005 Buxton et al.
2005/0240956 A1 10/2005 Smith et al.
2005/0246002 A1 11/2005 Martinez
2005/0256905 A1 11/2005 Gruhl et al.
2005/0261980 A1 11/2005 Hadi
2005/0267798 A1 12/2005 Panara
2005/0272017 A1 12/2005 Neuhauser et al.
2005/0273017 A1 12/2005 Gordon
2005/0273802 A1 12/2005 Crystal et al.
2005/0288954 A1 12/2005 McCarthy et al.
2005/0289582 A1 12/2005 Tavares et al.
2006/0003732 A1 1/2006 Neuhauser et al.
2006/0009702 A1 1/2006 Iwaki et al.
2006/0010470 A1 1/2006 Kurosaki et al.
2006/0035707 A1 2/2006 Nguyen et al.
2006/0041548 A1 2/2006 Parsons et al.
2006/0042483 A1 3/2006 Work et al.
2006/0053110 A1 3/2006 McDonald et al.
2006/0069663 A1 3/2006 Adar et al.
2006/0093998 A1 5/2006 Vertegaal
2006/0094934 A1 5/2006 Shirai et al.
2006/0111044 A1 5/2006 Keller
2006/0111644 A1 5/2006 Guttag et al.
2006/0129458 A1 6/2006 Maggio
2006/0149337 A1 7/2006 John
2006/0167376 A1 7/2006 Viirre et al.
2006/0168613 A1 7/2006 Wood et al.
2006/0168630 A1 7/2006 Davies
2006/0176289 A1 8/2006 Horn
2006/0189886 A1 8/2006 Jones et al.
2006/0190822 A1 8/2006 Basson et al.
2006/0218046 A1 9/2006 Carfi et al.
2006/0256133 A1 11/2006 Rosenberg
2006/0257834 A1 11/2006 Lee et al.
2006/0259360 A1 11/2006 Flinn et al.
2006/0259371 A1 11/2006 Perrier et al.
2006/0293921 A1 12/2006 McCarthy et al.
2007/0005752 A1 1/2007 Chawla et al.
2007/0016096 A1 1/2007 McNabb
2007/0038516 A1 2/2007 Apple et al.
2007/0048707 A1 3/2007 Caamano et al.
2007/0050256 A1 3/2007 Walker et al.
2007/0055169 A1 3/2007 Lee et al.
2007/0060830 A1 3/2007 Le et al.
2007/0060831 A1 3/2007 Le et al.
2007/0066874 A1 3/2007 Cook
2007/0066915 A1 3/2007 Frei et al.
2007/0066916 A1 3/2007 Lemos
2007/0067007 A1 3/2007 Schulman et al.
2007/0067305 A1 3/2007 Ives

(56) References Cited

U.S. PATENT DOCUMENTS

| | | | |
|---|---|---|---|
| 2007/0078700 | A1 | 4/2007 | Lenzmann et al. |
| 2007/0078706 | A1 | 4/2007 | Datta et al. |
| 2007/0079331 | A1 | 4/2007 | Datta et al. |
| 2007/0101360 | A1 | 5/2007 | Gutta et al. |
| 2007/0106170 | A1 | 5/2007 | Dunseath, Jr. et al. |
| 2007/0112460 | A1 | 5/2007 | Kiselik |
| 2007/0135727 | A1 | 6/2007 | Virtanen et al. |
| 2007/0135728 | A1 | 6/2007 | Snyder et al. |
| 2007/0136753 | A1 | 6/2007 | Bovenschulte et al. |
| 2007/0150281 | A1 | 6/2007 | Hoff |
| 2007/0150916 | A1 | 6/2007 | Begole et al. |
| 2007/0209047 | A1 | 9/2007 | Hallberg et al. |
| 2007/0214471 | A1 | 9/2007 | Rosenberg |
| 2007/0225585 | A1 | 9/2007 | Washbon et al. |
| 2007/0225674 | A1 | 9/2007 | Molnar et al. |
| 2007/0226760 | A1 | 9/2007 | Neuhauser et al. |
| 2007/0235716 | A1 | 10/2007 | Delic et al. |
| 2007/0238945 | A1 | 10/2007 | Delic et al. |
| 2007/0244977 | A1 | 10/2007 | Atkins |
| 2007/0250846 | A1 | 10/2007 | Swix et al. |
| 2007/0250901 | A1 | 10/2007 | McIntire et al. |
| 2007/0265507 | A1 | 11/2007 | de Lemos |
| 2007/0282566 | A1 | 12/2007 | Whitlow et al. |
| 2007/0294132 | A1 | 12/2007 | Zhang et al. |
| 2007/0294705 | A1 | 12/2007 | Gopalakrishnan et al. |
| 2007/0294706 | A1 | 12/2007 | Neuhauser et al. |
| 2008/0001600 | A1 | 1/2008 | deCharms |
| 2008/0004940 | A1 | 1/2008 | Rolleston Phillips |
| 2008/0010110 | A1 | 1/2008 | Neuhauser et al. |
| 2008/0024725 | A1 | 1/2008 | Todd |
| 2008/0027345 | A1 | 1/2008 | Kumada et al. |
| 2008/0040740 | A1 | 2/2008 | Plotnick et al. |
| 2008/0043013 | A1 | 2/2008 | Gruttadauria et al. |
| 2008/0059997 | A1 | 3/2008 | Plotnick et al. |
| 2008/0065468 | A1 | 3/2008 | Berg et al. |
| 2008/0065721 | A1 | 3/2008 | Cragun |
| 2008/0081961 | A1 | 4/2008 | Westbrook et al. |
| 2008/0082019 | A1 | 4/2008 | Ludving et al. |
| 2008/0086356 | A1 | 4/2008 | Glassman et al. |
| 2008/0091463 | A1 | 4/2008 | Shakamuri |
| 2008/0091512 | A1 | 4/2008 | Marci et al. |
| 2008/0097854 | A1 | 4/2008 | Young |
| 2008/0109840 | A1 | 5/2008 | Walter et al. |
| 2008/0125110 | A1 | 5/2008 | Ritter |
| 2008/0133724 | A1 | 6/2008 | Clark |
| 2008/0147448 | A1 | 6/2008 | Tunick et al. |
| 2008/0147742 | A1 | 6/2008 | Allen |
| 2008/0152300 | A1 | 6/2008 | Knee et al. |
| 2008/0162182 | A1 | 7/2008 | Cazares et al. |
| 2008/0177197 | A1 | 7/2008 | Lee et al. |
| 2008/0195471 | A1 | 8/2008 | Dube et al. |
| 2008/0204273 | A1 | 8/2008 | Crystal et al. |
| 2008/0208072 | A1 | 8/2008 | Fadem et al. |
| 2008/0214902 | A1 | 9/2008 | Lee et al. |
| 2008/0218472 | A1 | 9/2008 | Breen et al. |
| 2008/0221400 | A1 | 9/2008 | Lee et al. |
| 2008/0221472 | A1 | 9/2008 | Lee et al. |
| 2008/0221969 | A1 | 9/2008 | Lee et al. |
| 2008/0222670 | A1 | 9/2008 | Lee et al. |
| 2008/0222671 | A1 | 9/2008 | Lee et al. |
| 2008/0228077 | A1 | 9/2008 | Wilk et al. |
| 2008/0249865 | A1 | 10/2008 | Angell et al. |
| 2008/0255949 | A1 | 10/2008 | Genco et al. |
| 2008/0263458 | A1 | 10/2008 | Altberg et al. |
| 2008/0295126 | A1 | 11/2008 | Lee et al. |
| 2009/0018996 | A1 | 1/2009 | Hunt et al. |
| 2009/0024049 | A1 | 1/2009 | Pradeep et al. |
| 2009/0024448 | A1 | 1/2009 | Pradeep et al. |
| 2009/0024449 | A1 | 1/2009 | Pradeep et al. |
| 2009/0024475 | A1 | 1/2009 | Pradeep et al. |
| 2009/0025023 | A1 | 1/2009 | Pradeep et al. |
| 2009/0025024 | A1 | 1/2009 | Beser et al. |
| 2009/0030287 | A1 | 1/2009 | Pradeep et al. |
| 2009/0030303 | A1 | 1/2009 | Pradeep et al. |
| 2009/0030717 | A1 | 1/2009 | Pradeep et al. |
| 2009/0030762 | A1 | 1/2009 | Lee et al. |
| 2009/0030780 | A1 | 1/2009 | York et al. |
| 2009/0030930 | A1 | 1/2009 | Pradeep et al. |
| 2009/0036755 | A1 | 2/2009 | Pradeep et al. |
| 2009/0036756 | A1 | 2/2009 | Pradeep et al. |
| 2009/0037575 | A1 | 2/2009 | Crystal et al. |
| 2009/0060240 | A1 | 3/2009 | Coughlan et al. |
| 2009/0062629 | A1 | 3/2009 | Pradeep et al. |
| 2009/0062679 | A1 | 3/2009 | Tan et al. |
| 2009/0062680 | A1 | 3/2009 | Sandford |
| 2009/0062681 | A1 | 3/2009 | Pradeep et al. |
| 2009/0063255 | A1 | 3/2009 | Pradeep et al. |
| 2009/0063256 | A1 | 3/2009 | Pradeep et al. |
| 2009/0069652 | A1 | 3/2009 | Lee et al. |
| 2009/0070798 | A1 | 3/2009 | Lee et al. |
| 2009/0082643 | A1 | 3/2009 | Pradeep et al. |
| 2009/0082689 | A1 | 3/2009 | Guttag et al. |
| 2009/0083129 | A1 | 3/2009 | Pradeep et al. |
| 2009/0088610 | A1 | 4/2009 | Lee et al. |
| 2009/0089830 | A1 | 4/2009 | Chandmtillake et al. |
| 2009/0094286 | A1 | 4/2009 | Lee et al. |
| 2009/0094627 | A1 | 4/2009 | Lee et al. |
| 2009/0094628 | A1 | 4/2009 | Lee et al. |
| 2009/0094629 | A1 | 4/2009 | Lee et al. |
| 2009/0097689 | A1 | 4/2009 | Prest et al. |
| 2009/0112077 | A1 | 4/2009 | Nguyen et al. |
| 2009/0131764 | A1 | 5/2009 | Lee et al. |
| 2009/0132441 | A1 | 5/2009 | Muller et al. |
| 2009/0133047 | A1 | 5/2009 | Lee et al. |
| 2009/0138356 | A1 | 5/2009 | Pomplun |
| 2009/0150919 | A1 | 6/2009 | Lee et al. |
| 2009/0153328 | A1 | 6/2009 | Otani et al. |
| 2009/0158308 | A1 | 6/2009 | Weitzenfeld et al. |
| 2009/0163777 | A1 | 6/2009 | Jung et al. |
| 2009/0024447 | A1 | 7/2009 | Pradeep et al. |
| 2009/0195392 | A1 | 8/2009 | Zalewski |
| 2009/0214060 | A1 | 8/2009 | Chuang et al. |
| 2009/0221928 | A1 | 9/2009 | Einav et al. |
| 2009/0248484 | A1 | 10/2009 | Surendran et al. |
| 2009/0248496 | A1 | 10/2009 | Hueter et al. |
| 2009/0253996 | A1 | 10/2009 | Lee et al. |
| 2009/0259137 | A1 | 10/2009 | Delic et al. |
| 2009/0259509 | A1 | 10/2009 | Landvater |
| 2009/0271294 | A1 | 10/2009 | Hadi |
| 2009/0292587 | A1 | 11/2009 | Fitzgerald |
| 2009/0300672 | A1 | 12/2009 | Van Gulik |
| 2009/0305006 | A1 | 12/2009 | Steffen |
| 2009/0318773 | A1 | 12/2009 | Jung et al. |
| 2009/0318826 | A1 | 12/2009 | Green et al. |
| 2009/0327068 | A1 | 12/2009 | Pradeep et al. |
| 2009/0328089 | A1 | 12/2009 | Pradeep et al. |
| 2010/0004977 | A1 | 1/2010 | Marci et al. |
| 2010/0022821 | A1 | 1/2010 | Dubi et al. |
| 2010/0041962 | A1 | 2/2010 | Causevic et al. |
| 2010/0060300 | A1 | 3/2010 | Muller et al. |
| 2010/0094702 | A1 | 4/2010 | Silberstein |
| 2010/0125219 | A1 | 5/2010 | Harris et al. |
| 2010/0145176 | A1 | 6/2010 | Himes |
| 2010/0145215 | A1 | 6/2010 | Pradeep et al. |
| 2010/0145217 | A1 | 6/2010 | Otto et al. |
| 2010/0180029 | A1 | 7/2010 | Fourman |
| 2010/0183279 | A1 | 7/2010 | Pradeep et al. |
| 2010/0186031 | A1 | 7/2010 | Pradeep et al. |
| 2010/0186032 | A1 | 7/2010 | Pradeep et al. |
| 2010/0198042 | A1 | 8/2010 | Popescu et al. |
| 2010/0214318 | A1 | 8/2010 | Pradeep et al. |
| 2010/0215289 | A1 | 8/2010 | Pradeep et al. |
| 2010/0218208 | A1 | 8/2010 | Holden |
| 2010/0228604 | A1 | 9/2010 | Desai et al. |
| 2010/0249538 | A1 | 9/2010 | Pradeep et al. |
| 2010/0249636 | A1 | 9/2010 | Pradeep et al. |
| 2010/0250325 | A1 | 9/2010 | Pradeep et al. |
| 2010/0250458 | A1 | 9/2010 | Ho |
| 2010/0257052 | A1 | 10/2010 | Zito et al. |
| 2010/0268540 | A1 | 10/2010 | Arshi et al. |
| 2010/0268573 | A1 | 10/2010 | Jain et al. |
| 2010/0269127 | A1 | 10/2010 | Krug |
| 2010/0274152 | A1 | 10/2010 | McPeck et al. |
| 2010/0274153 | A1 | 10/2010 | Tucker et al. |

(56) References Cited

U.S. PATENT DOCUMENTS

| | | | |
|---|---|---|---|
| 2010/0292998 | A1 | 11/2010 | Bodlaender et al. |
| 2010/0306120 | A1 | 12/2010 | Ciptawilangga |
| 2010/0317988 | A1 | 12/2010 | Terada et al. |
| 2010/0325660 | A1 | 12/2010 | Holden |
| 2010/0331661 | A1 | 12/2010 | Nakagawa |
| 2011/0004089 | A1 | 1/2011 | Chou |
| 2011/0015503 | A1 | 1/2011 | Joffe et al. |
| 2011/0040202 | A1 | 2/2011 | Luo et al. |
| 2011/0046473 | A1 | 2/2011 | Pradeep et al. |
| 2011/0046502 | A1 | 2/2011 | Pradeep et al. |
| 2011/0046503 | A1 | 2/2011 | Pradeep et al. |
| 2011/0046504 | A1 | 2/2011 | Pradeep et al. |
| 2011/0047121 | A1 | 2/2011 | Pradeep et al. |
| 2011/0059422 | A1 | 3/2011 | Masaoka |
| 2011/0085700 | A1 | 4/2011 | Lee |
| 2011/0098593 | A1 | 4/2011 | Low et al. |
| 2011/0105937 | A1 | 5/2011 | Pradeep et al. |
| 2011/0106621 | A1 | 5/2011 | Pradeep et al. |
| 2011/0106750 | A1 | 5/2011 | Pradeep et al. |
| 2011/0119124 | A1 | 5/2011 | Pradeep et al. |
| 2011/0119129 | A1 | 5/2011 | Pradeep et al. |
| 2011/0131274 | A1 | 6/2011 | Hille |
| 2011/0144519 | A1 | 6/2011 | Causevic |
| 2011/0153391 | A1 | 6/2011 | Tenbrock |
| 2011/0208515 | A1 | 8/2011 | Neuhauser |
| 2011/0224569 | A1 | 9/2011 | Isenhart et al. |
| 2011/0237923 | A1 | 9/2011 | Picht et al. |
| 2011/0237971 | A1 | 9/2011 | Pradeep et al. |
| 2011/0248729 | A2 | 10/2011 | Mueller et al. |
| 2011/0257502 | A1 | 10/2011 | Lee |
| 2011/0257937 | A1 | 10/2011 | Lee |
| 2011/0270620 | A1 | 11/2011 | Pradeep et al. |
| 2011/0276504 | A1 | 11/2011 | Pradeep et al. |
| 2011/0282231 | A1 | 11/2011 | Pradeep et al. |
| 2011/0282232 | A1 | 11/2011 | Pradeep et al. |
| 2011/0282749 | A1 | 11/2011 | Pradeep et al. |
| 2011/0298706 | A1 | 12/2011 | Mann |
| 2011/0319975 | A1 | 12/2011 | Ho et al. |
| 2012/0004899 | A1 | 1/2012 | Arshi |
| 2012/0022391 | A1 | 1/2012 | Leuthardt |
| 2012/0036004 | A1 | 2/2012 | Pradeep et al. |
| 2012/0036005 | A1 | 2/2012 | Pradeep et al. |
| 2012/0046993 | A1 | 2/2012 | Hill |
| 2012/0054018 | A1 | 3/2012 | Pradeep et al. |
| 2012/0072289 | A1 | 3/2012 | Pradeep et al. |
| 2012/0083668 | A1 | 4/2012 | Pradeep et al. |
| 2012/0084139 | A1 | 4/2012 | Pradeep et al. |
| 2012/0108995 | A1 | 5/2012 | Pradeep et al. |
| 2012/0114305 | A1 | 5/2012 | Holden |
| 2012/0130800 | A1 | 5/2012 | Pradeep et al. |
| 2012/0173701 | A1 | 7/2012 | Tenbrock |
| 2012/0203363 | A1 | 8/2012 | McKenna et al. |
| 2012/0203559 | A1 | 8/2012 | McKenna et al. |
| 2012/0239407 | A1 | 9/2012 | Lynch et al. |
| 2012/0245978 | A1 | 9/2012 | Jain et al. |
| 2012/0284112 | A1 | 11/2012 | Pradeep et al. |
| 2012/0284332 | A1 | 11/2012 | Pradeep et al. |
| 2012/0290409 | A1 | 11/2012 | Pradeep et al. |
| 2013/0024272 | A1 | 1/2013 | Pradeep et al. |
| 2013/0046577 | A1 | 2/2013 | Marci et al. |
| 2013/0124365 | A1 | 5/2013 | Pradeep |
| 2013/0124623 | A1 | 5/2013 | Munter |
| 2013/0152506 | A1 | 6/2013 | Pradeep |
| 2013/0166373 | A1 | 6/2013 | Pradeep et al. |
| 2013/0185140 | A1 | 7/2013 | Pradeep et al. |
| 2013/0185141 | A1 | 7/2013 | Pradeep et al. |
| 2013/0185142 | A1 | 7/2013 | Pradeep et al. |
| 2013/0185144 | A1 | 7/2013 | Pradeep et al. |
| 2013/0185145 | A1 | 7/2013 | Pradeep et al. |
| 2013/0304540 | A1 | 11/2013 | Pradeep et al. |
| 2013/0332259 | A1 | 12/2013 | Pradeep et al. |
| 2017/0039591 | A1 | 2/2017 | Knight et al. |
| 2018/0247332 | A1 | 8/2018 | Pradeep et al. |
| 2018/0341977 | A1 | 11/2018 | Knight et al. |
| 2019/0005532 | A1 | 1/2019 | Pradeep et al. |
| 2019/0034958 | A1 | 1/2019 | Pradeep et al. |
| 2019/0034959 | A1 | 1/2019 | Pradeep et al. |
| 2019/0139078 | A1 | 5/2019 | Pradeep et al. |
| 2019/0156352 | A1 | 5/2019 | Pradeep et al. |
| 2019/0220888 | A1 | 7/2019 | Knight et al. |
| 2019/0282153 | A1 | 9/2019 | Pradeep et al. |
| 2020/0005339 | A1 | 1/2020 | Pradeep et al. |
| 2020/0163571 | A1 | 5/2020 | Pradeep et al. |
| 2020/0211033 | A1 | 7/2020 | Pradeep et al. |
| 2020/0234329 | A1 | 7/2020 | Pradeep et al. |
| 2020/0258116 | A1 | 8/2020 | Pradeep et al. |
| 2020/0364741 | A1 | 11/2020 | Pradeep et al. |

FOREIGN PATENT DOCUMENTS

| | | |
|---|---|---|
| GB | 1374658 | 11/1974 |
| GB | 2221759 | 2/1990 |
| JP | 2001147944 | 5/2001 |
| JP | 2005-160805 | 12/2003 |
| JP | 2005051654 | 2/2005 |
| JP | 2006006355 | 1/2006 |
| JP | 2006227994 | 8/2006 |
| JP | 2006-305334 | 11/2006 |
| JP | 2007310454 | 11/2007 |
| KR | 200422399 | 7/2006 |
| WO | 95-018565 | 7/1995 |
| WO | 1997-017774 | 5/1997 |
| WO | 1997-040745 | 11/1997 |
| WO | 1997-041673 | 11/1997 |
| WO | 02-100241 | 12/2002 |
| WO | 02-102238 | 12/2002 |
| WO | 2004-049225 | 6/2004 |
| WO | 2006-009771 | 1/2006 |
| WO | 2008030831 | 3/2008 |
| WO | 2008055078 | 5/2008 |
| WO | 2008-064431 | 6/2008 |
| WO | 2008072739 | 6/2008 |
| WO | 2008-077178 | 7/2008 |
| WO | 2008-109694 | 9/2008 |
| WO | 2008-109699 | 9/2008 |
| WO | 2008-121651 | 10/2008 |
| WO | 2008-137579 | 11/2008 |
| WO | 2008-137581 | 11/2008 |
| WO | 2008-141340 | 11/2008 |
| WO | 2008-154410 | 12/2008 |
| WO | 2009-018374 | 2/2009 |
| WO | 2009-052833 | 4/2009 |
| WO | 2011-055291 | 5/2011 |
| WO | 2011-056679 | 5/2011 |

OTHER PUBLICATIONS

Office Action, issued by the United States Patent and Trademark Office in connection with U.S. Appl. No. 12/056,211, dated Jan. 7, 2011, 19 pages.

Office Action issued by the United States Patent and Trademark Office in connection with U.S. Appl. No. 12/056,221, dated Apr. 15, 2011, 24 pages.

Final Rejection, issued by the United States Patent and Trademark Office in connection with U.S. Appl. No. 12/113,863, dated Jun. 9, 2011, 12 pages.

Office Action, issued by the United States Patent and Trademark Office in connection with U.S. Appl. No. 12/113,863, dated Dec. 27, 2010, 15 pages.

Final Rejection, issued by the United States Patent and Trademark Office in connection with U.S. Appl. No. 12/113,870, dated Apr. 21, 2011, 10 pages.

Office Action, issued by the United States Patent and Trademark Office in connection with U.S. Appl. No. 12/113,870, dated Dec. 3, 2010, 12 pages.

Office Action, issued by the United States Patent and Trademark Office in connection with U.S. Appl. No. 12/122,240, dated Jun. 10, 2011, 12 pages.

Final Rejection, issued by the United States Patent and Trademark Office in connection with U.S. Appl. No. 12/122,262, dated May 26, 2011, 15 pages.

(56) References Cited

OTHER PUBLICATIONS

Office Action, issued by the United States Patent and Trademark Office in connection with U.S. Appl. No. 12/122,262, dated Dec. 9, 2010, 13 pages.
Final Rejection, issued by the United States Patent and Trademark Office in connection with U.S. Appl. No. 12/135,066, dated Jan. 21, 2011, 16 pages.
Office Action, issued by the United States Patent and Trademark Office in connection with U.S. Appl. No. 12/135,066, dated Oct. 28, 2010, 14 pages.
Notice of Panel Decision from Pre-Appeal Brief Review, issued by the United States Patent and Trademark Office in connection with U.S. Appl. No. 12/135,066, dated May 31, 2011, 2 pages.
Office Action, issued by the United States Patent and Trademark Office in connection with U.S. Appl. No. 12/135,074, dated Dec. 23, 2010, 14 pages.
Final Rejection, issued by the United States Patent and Trademark Office in connection with U.S. Appl. No. 12/135,074, dated Jun. 9, 2011, 10 pages.
Final Rejection, issued by the United States Patent and Trademark Office in connection with U.S. Appl. No. 12/182,874, dated Jul. 7, 2011, 14 pages.
Office Action, issued by the United States Patent and Trademark Office in connection with U.S. Appl. No. 12/182,874, dated Dec. 27, 2010, 17 pages.
Office Action, issued by the United States Patent and Trademark Office in connection with U.S. Appl. No. 12/199,557, dated Dec. 27, 2010, 14 pages.
Final Rejection, issued by the United States Patent and Trademark Office in connection with U.S. Appl. No. 12/199,557, dated Jun. 9, 2011, 12 pages.
Final Rejection, issued by the United States Patent and Trademark Office in connection with U.S. Appl. No. 12/199,583, dated Jun. 21, 2011, 14 pages.
Office Action, issued by the United States Patent and Trademark Office in connection with U.S. Appl. No. 12/199,583, dated Dec. 27, 2010, 17 pages.
Final Rejection, issued by the United States Patent and Trademark Office in connection with U.S. Appl. No. 12/199,596, dated Jun. 14, 2011, 13 pages.
Office Action, issued by the United States Patent and Trademark Office in connection with U.S. Appl. No. 12/199,596, dated Dec. 27, 2010, 17 pages.
Final Rejection, issued by the United States Patent and Trademark Office in connection with U.S. Appl. No. 12/200,813, dated Jul. 6, 2011, 13 pages.
Office Action, issued by the United States Patent and Trademark Office in connection with U.S. Appl. No. 12/200,813, dated Dec. 27, 2010, 14 pages.
Office Action, issued by the United States Patent and Trademark Office in connection with U.S. Appl. No. 12/234,372, dated Jun. 7, 2011, 10 pages.
Final Rejection, issued by the United States Patent and Trademark Office in connection with U.S. Appl. No. 12/135,069, dated Feb. 17, 2011, 32 pages.
Office Action, issued by the United States Patent and Trademark Office in connection with U.S. Appl. No. 12/135,069, dated Oct. 29, 2010, 21 pages.
Office Action, issued by the United States Patent and Trademark Office in connection with U.S. Appl. No. 12/357,315, dated May 4, 2011, 9 pages.
Office Action, issued by the United States Patent and Trademark Office in connection with U.S. Appl. No. 12/410,380, dated Jun. 7, 2011, 9 pages.
Office Action, issued by the United States Patent and Trademark Office in connection with U.S. Appl. No. 12/413,297, dated Jul. 18, 2011, 9 pages.
Office Action, issued by the United States Patent and Trademark Office in connection with U.S. Appl. No. 12/608,685,dated Jul. 12, 2011, 15 pages.
Office Action, issued by the United States Patent and Trademark Office in connection with U.S. Appl. No. 12/056,190,dated Aug. 10, 2011, 28 pages.
Office Action, issued by the United States Patent and Trademark Office in connection with U.S. Appl. No. 12/357,322,dated Aug. 23, 2011, 12 pages.
Office Action, issued by the United States Patent and Trademark Office in connection with U.S. Appl. No. 12/135,069,dated Aug. 26, 2011, 33 pages.
Restriction Requirement, issued by the United States Patent and Trademark Office in connection with U.S. Appl. No. 12/122,253,dated Sep. 2, 2011, 7 pages.
Office Action, issued by the United States Patent and Trademark Office in connection with U.S. Appl. No. 12/410,372, dated Sep. 12, 2011, 12 pages.
Restriction Requirement, issued by the United States Patent and Trademark Office in connection with U.S. Appl. No. 12/182,851, dated Sep. 12, 2011, 7 pages.
Office Action, issued by the United States Patent and Trademark Office in connection with U.S. Appl. No. 12/135,066, dated Sep. 29, 2011, 37 pages.
Restriction Requirement, issued by the United States Patent and Trademark Office in connection with U.S. Appl. No. 12/056,225, dated Oct. 3, 2011, 6 pages.
Office Action, issued by the United States Patent and Trademark Office in connection with U.S. Appl. No. 12/234,388, dated Oct. 12, 2011, 27 pages.
Office Action, issued by the United States Patent and Trademark Office in connection with U.S. Appl. No. 12/234,372, dated Oct. 13, 2011, 22 pages.
Office Action, issued by the United States Patent and Trademark Office in connection with U.S. Appl. No. 12/410,380, dated Oct. 19, 2011, 21 pages.
Office Action, issued by the United States Patent and Trademark Office in connection with U.S. Appl. No. 12/357,315, dated Oct. 26, 2011, 41 pages.
Office Action, issued by the United States Patent and Trademark Office in connection with U.S. Appl. No. 12/122,240, dated Oct. 27, 2011, 39 pages.
Final Rejection, issued by the United States Patent and Trademark Office in connection with U.S. Appl. No. 12/056,221, dated Nov. 28, 2011, 44 pages.
Office Action, issued by the United States Patent and Trademark Office in connection with U.S. Appl. No. 12/608,660, dated Dec. 7, 2011, 8 pages.
Office Action, issued by the United States Patent and Trademark Office in connection with U.S. Appl. No. 12/113,863, dated Dec. 22, 2011, 17 pages.
Office Action, issued by the United States Patent and Trademark Office in connection with U.S. Appl. No. 12/122,262, dated Dec. 22, 2011, 17 pages.
Office Action, issued by the United States Patent and Trademark Office in connection with U.S. Appl. No. 12/135,074, dated Dec. 22, 2011, 16 pages.
Office Action, issued by the United States Patent and Trademark Office in connection with U.S. Appl. No. 12/199,557, dated Dec. 22, 2011, 17 pages.
Office Action, issued by the United States Patent and Trademark Office in connection with U.S. Appl. No. 12/199,596, dated Dec. 22, 2011, 15 pages.
Office Action, issued by the United States Patent and Trademark Office in connection with U.S. Appl. No. 12/200,813, dated Dec. 22, 2011, 18 pages.
Office Action, issued by the United States Patent and Trademark Office in connection with U.S. Appl. No. 12/199,583, dated Dec. 29, 2011, 18 pages.
Final Rejection, issued by the United States Patent and Trademark Office in connection with U.S. Appl. No. 12/410,372, dated Jan. 3, 2012, 10 pages.
Final Rejection, issued by the United States Patent and Trademark Office in connection with U.S. Appl. No. 12/413,297, dated Jan. 4, 2012, 10 pages.

(56) References Cited

OTHER PUBLICATIONS

Office Action, issued by the United States Patent and Trademark Office in connection with U.S. Appl. No. 12/544,921, dated Jan. 9, 2012, 13 pages.
Office Action, issued by the United States Patent and Trademark Office in connection with U.S. Appl. No. 12/357,302, dated Jan. 17, 2012, 11 pages.
Office Action, issued by the United States Patent and Trademark Office in connection with U.S. Appl. No. 12/056,225, dated Jan. 20, 2012, 12 pages.
Final Rejection, issued by the United States Patent and Trademark Office in connection with U.S. Appl. No. 12/135,066, dated Jan. 24, 2012, 12 pages.
Office Action, issued by the United States Patent and Trademark Office in connection with U.S. Appl. No. 12/546,586, dated Feb. 1, 2012, 17 pages.
Restriction Requirement, issued by the United States Patent and Trademark Office in connection with U.S. Appl. No. 12/544,958, dated Feb. 10, 2012, 6 pages.
Final Rejection, issued by the United States Patent and Trademark Office in connection with U.S. Appl. No. 12/135,069, dated Feb. 14, 2012, 36 pages.
Final Rejection, issued by the United States Patent and Trademark Office in connection with U.S. Appl. No. 12/357,322, dated Feb. 14, 2012, 14 pages.
Office Action, issued by the United States Patent and Trademark Office in connection with U.S. Appl. No. 12/056,211, dated Feb. 16, 2012, 16 pages.
Final Rejection, issued by the United States Patent and Trademark Office in connection with U.S. Appl. No. 12/056,190, dated Feb. 17, 2012, 22 pages.
Office Action, issued by the United States Patent and Trademark Office in connection with U.S. Appl. No. 12/122,253, dated Feb. 17, 2012, 20 pages.
Office Action, issued by the United States Patent and Trademark Office in connection with U.S. Appl. No. 12/182,874, dated Feb. 17, 2012, 15 pages.
Office Action, issued by the United States Patent and Trademark Office in connection with U.S. Appl. No. 12/868,531, dated Mar. 1, 2012, 7 pages.
Office Action, issued by the United States Patent and Trademark Office in connection with U.S. Appl. No. 12/182,851, dated Mar. 14, 2012, 17 pages.
Office Action, issued by the United States Patent and Trademark Office in connection with U.S. Appl. No. 12/608,685, dated Mar. 29, 2012, 17 pages.
Office Action, issued by the United States Patent and Trademark Office in connection with U.S. Appl. No. 12/846,242, dated Mar. 29, 2012, 16 pages.
Office Action, issued by the United States Patent and Trademark Office in connection with U.S. Appl. No. 12/234,388, dated Apr. 6, 2012, 6 pages.
Office Action, issued by the United States Patent and Trademark Office in connection with U.S. Appl. No. 12/357,315, dated Apr. 9, 2012, 17 pages.
Office Action, issued by the United States Patent and Trademark Office in connection with U.S. Appl. No. 12/544,958, dated May 2, 2012, 15 pages.
Notice of Allowance, issued by the United States Patent and Trademark Office in connection with U.S. Appl. No. 12/357,302, dated May 7, 2012, 11 pages.
Notice of Allowance, issued by the United States Patent and Trademark Office in connection with U.S. Appl. No. 12/868,531, dated May 8, 2012, 11 pages.
Notice of Allowance, issued by the United States Patent and Trademark Office in connection with U.S. Appl. No. 12/608,696, dated May 15, 2012, 6 pages.
Restriction Requirement, issued by the United States Patent and Trademark Office in connection with U.S. Appl. No. 12/545,455, dated Jun. 13, 2012, 5 pages.
Office Action, issued by the United States Patent and Trademark Office in connection with U.S. Appl. No. 12/056,225, dated Jun. 15, 2012, 9 pages.
Office Action, issued by the United States Patent and Trademark Office in connection with U.S. Appl. No. 12/544,934, dated Jun. 18, 2012, 11 pages.
Office Action, issued by the United States Patent and Trademark Office in connection with U.S. Appl. No. 12/135,066, dated Jun. 21, 2012, 10 pages.
Final Rejection, issued by the United States Patent and Trademark Office in connection with U.S. Appl. No. 12/608,660, dated Jul. 10, 2012, 14 pages.
Final Rejection, issued by the United States Patent and Trademark Office in connection with U.S. Appl. No. 12/608,685, dated Jul. 30, 2012, 15 pages.
Examiner's Answer, issued by the United States Patent and Trademark Office in connection with U.S. Appl. No. 12/410,372, dated Aug. 3, 2012, 8 pages.
Examiner's Answer, issued by the United States Patent and Trademark Office in connection with U.S. Appl. No. 12/410,380, dated Jun. 8, 2012, 12 pages.
Examiner's Answer, issued by the United States Patent and Trademark Office in connection with U.S. Appl. No. 12/234,372, dated May 23, 2012, 11 pages.
Advisory Action, issued by the United States Patent and Trademark Office in connection with U.S. Appl. No. 12/234,388, dated Aug. 28, 2012, 3 pages.
Office Action, issued by the United States Patent and Trademark Office in connection with U.S. Appl. No. 12/545,455, dated Aug. 29, 2012, 11 pages.
Office Action, issued by the United States Patent and Trademark Office in connection with U.S. Appl. No. 12/778,828, dated Aug. 30, 2012, 9 pages.
Office Action, issued by the United States Patent and Trademark Office in connection with U.S. Appl. No. 12/778,810, dated Aug. 31, 2012, 12 pages.
Notice of Allowance, issued by the United States Patent and Trademark Office in connection with U.S. Appl. No. 12/056,190, dated Sep. 17, 2012, 11 pages.
Notice of Allowance, issued by the United States Patent and Trademark Office in connection with U.S. Appl. No. 12/122,262, dated Sep. 17, 2012, 11 pages.
Final Rejection, issued by the United States Patent and Trademark Office in connection with U.S. Appl. No. 12/122,253, dated Sep. 17, 2012, 17 pages.
Examiner's Answer, issued by the United States Patent and Trademark Office in connection with U.S. Appl. No. 12/413,297, dated Sep. 18, 2012, 18 pages.
Final Rejection, issued by the United States Patent and Trademark Office in connection with U.S. Appl. No. 12/546,586, dated Sep. 18, 2012, 17 pages.
Notice of Allowance, issued by the United States Patent and Trademark Office in connection with U.S. Appl. No. 12/056,211, dated Sep. 19, 2012, 10 pages.
Notice of Allowance, issued by the United States Patent and Trademark Office in connection with U.S. Appl. No. 12/135,074, dated Sep. 19, 2012, 10 pages.
Notice of Allowance, issued by the United States Patent and Trademark Office in connection with U.S. Appl. No. 12/853,213, dated Sep. 7, 2012, 9 pages.
Notice of Allowance, issued by the United States Patent and Trademark Office in connection with U.S. Appl. No. 12/199,583, dated Sep. 26, 2012, 14 pages.
Notice of Allowance, issued by the United States Patent and Trademark Office in connection with U.S. Appl. No. 12/199,596, dated Sep. 27, 2012, 14 pages.
Notice of Allowance, issued by the United States Patent and Trademark Office in connection with U.S. Appl. No. 12/199,557, dated Sep. 28, 2012, 12 pages.
Notice of Allowance, issued by the United States Patent and Trademark Office in connection with U.S. Appl. No. 12/113,863, dated Oct. 1, 2012, 12 pages.

(56) References Cited

OTHER PUBLICATIONS

Office Action, issued by the United States Patent and Trademark Office in connection with U.S. Appl. No. 13/444,149, dated Oct. 4, 2012, 9 pages.
Final Office Action, issued by the United States Patent and Trademark Office in connection with U.S. Appl. No. 12/182,851, dated Oct. 4, 2012, 14 pages.
Office Action, issued by the United States Patent and Trademark Office in connection with U.S. Appl. No. 12/234,388, dated Oct. 5, 2012, 6 pages.
Notice of Allowance, issued by the United States Patent and Trademark Office in connection with U.S. Appl. No. 12/853,197, dated Oct. 16, 2012, 5 pages.
Notice of Allowance, issued by the United States Patent and Trademark Office in connection with U.S. Appl. No. 12/868,531, dated Oct. 22, 2012, 5 pages.
Final Office Action, issued by the United States Patent and Trademark Office in connection with U.S. Appl. No. 12/846,242, dated Nov. 29, 2012, 14 pages.
Notice of Allowance, issued by the United States Patent and Trademark Office in connection with U.S. Appl. No. 12/200,813, dated Oct. 30, 2012, 5 pages.
Notice of Allowance, issued by the United States Patent and Trademark Office in connection with U.S. Appl. No. 12/056,190, dated Nov. 2, 2012, 5 pages.
Restriction Requirement, issued by the United States Patent and Trademark Office in connection with U.S. Appl. No. 12/056,225, dated Nov. 2, 2012, 5 pages.
Final Office Action, issued by the United States Patent and Trademark Office in connection with U.S. Appl. No. 12/135,066, dated Nov. 13, 2012, 9 pages.
Notice of Allowance, issued by the United States Patent and Trademark Office in connection with U.S. Appl. No. 12/113,863, dated Nov. 16, 2012, 5 pages.
Notice of Allowance, issued by the United States Patent and Trademark Office in connection with U.S. Appl. No. 12/056,211, dated Nov. 21, 2012, 5 pages.
Notice of Allowance, issued by the United States Patent and Trademark Office in connection with U.S. Appl. No. 12/868,531, dated Nov. 23, 2012, 5 pages.
Office Action, issued by the United States Patent and Trademark Office in connection with U.S. Appl. No. 12/913,102, dated Dec. 7, 2012, 7 pages.
Final Office Action, issued by the United States Patent and Trademark Office in connection with U.S. Appl. No. 12/544,958, dated Dec. 10, 2012, 16 pages.
Notice of Allowance, issued by the United States Patent and Trademark Office in connection with U.S. Appl. No. 12/853,197, dated Dec. 20, 2012, 5 pages.
Notice of Allowance, issued by the United States Patent and Trademark Office in connection with U.S. Appl. No. 12/056,190, dated Dec. 21, 2012, 14 pages.
Notice of Allowance, issued by the United States Patent and Trademark Office in connection with U.S. Appl. No. 12/056,211, dated Dec. 21, 2012, 10 pages.
Notice of Allowance, issued by the United States Patent and Trademark Office in connection with U.S. Appl. No. 12/122,262, dated Dec. 21, 2012, 19 pages.
Notice of Allowance, issued by the United States Patent and Trademark Office in connection with U.S. Appl. No. 12/135,074, dated Dec. 21, 2012, 12 pages.
Notice of Allowance, issued by the United States Patent and Trademark Office in connection with U.S. Appl. No. 12/199,557, dated Dec. 21, 2012, 14 pages.
Notice of Allowance, issued by the United States Patent and Trademark Office in connection with U.S. Appl. No. 12/199,596, dated Dec. 21, 2012, 17 pages.
Notice of Allowance, issued by the United States Patent and Trademark Office in connection with U.S. Appl. No. 12/200,813, dated Dec. 21, 2012, 9 pages.
Notice of Allowance, issued by the United States Patent and Trademark Office in connection with U.S. Appl. No. 12/853,213, dated Dec. 21, 2012, 10 pages.
Notice of Allowance, issued by the United States Patent and Trademark Office in connection with U.S. Appl. No. 12/868,531, dated Dec. 26, 2012, 2 pages.
Notice of Allowance, issued by the United States Patent and Trademark Office in connection with U.S. Appl. No. 12/113,863, dated Dec. 31, 2012, 5 pages.
Notice of Allowance, issued by the United States Patent and Trademark Office in connection with U.S. Appl. No. 12/199,583, dated Dec. 31, 2012, 10 pages.
Final Office Action, issued by the United States Patent and Trademark Office in connection with U.S. Appl. No. 12/182,874, dated Jan. 4, 2013, 17 pages.
Notice of Allowance, issued by the United States Patent and Trademark Office in connection with U.S. Appl. No. 12/199,583, dated Jan. 11, 2013, 11 pages.
Final Office Action, issued by the United States Patent and Trademark Office in connection with U.S. Appl. No. 12/056,225, dated Jan. 11, 2013, 11 pages.
Recertified IDS and Interview Summary, issued by the United States Patent and Trademark Office in connection with U.S. Appl. No. 12/853,197, dated Jan. 16, 2013, 6 pages.
Notice of Allowance, issued by the United States Patent and Trademark Office in connection with U.S. Appl. No. 12/199,557, dated Jan. 29, 2013, 17 pages.
Notice of Allowance, issued by the United States Patent and Trademark Office in connection with U.S. Appl. No. 12/85,3197, dated Jan. 29, 2013, 11 pages.
Notice of Allowance, issued by the United States Patent and Trademark Office in connection with U.S. Appl. No. 12/056,190, dated Jan. 31, 2013, 5 pages.
Notice of Allowance, issued by the United States Patent and Trademark Office in connection with U.S. Appl. No. 12/113,863, dated Jan. 31,2013, 5 pages.
Notice of Allowance, issued by the United States Patent and Trademark Office in connection with U.S. Appl. No. 12/135,074, dated Jan. 31, 2013, 10 pages.
Notice of Allowance, issued by the United States Patent and Trademark Office in connection with U.S. Appl. No. 12/199,583, dated Feb. 1, 2013, 11 pages.
Notice of Allowance, issued by the United States Patent and Trademark Office in connection with U.S. Appl. No. 12/200,813, dated Feb. 1, 2013, 5pages.
Notice of Allowance, issued by the United States Patent and Trademark Office in connection with U.S. Appl. No. 12/056,211, dated Feb. 4, 2013, 5 pages.
Notice of Allowance, issued by the United States Patent and Trademark Office in connection with U.S. Appl. No. 12/122,262, dated Feb. 5, 2013, 15 pages.
Notice of Allowance, issued by the United States Patent and Trademark Office in connection with U.S. Appl. No. 12/868,531, dated Feb. 5, 2013, 8 pages.
Notice of Allowance, issued by the United States Patent and Trademark Office in connection with U.S. Appl. No. 12/853,213, dated Feb. 5, 2013, 10 pages.
Notice of Allowance, issued by the United States Patent and Trademark Office in connection with U.S. Appl. No. 12/234,388, dated Feb. 15, 2013, 9 pages.
Notice of Allowance, issued by the United States Patent and Trademark Office in connection with U.S. Appl. No. 12/056,190, dated Feb. 14, 2013, 5 pages.
Notice of Allowance, issued by the United States Patent and Trademark Office in connection with U.S. Appl. No. 12/200,813, dated Sep. 20, 2012, 11 pages.
Notice of Allowance, issued by the United States Patent and Trademark Office in connection with U.S. Appl. No. 12/182,874, dated Apr. 16, 2013, 10 pages.
Notice of Allowance, issued by the United States Patent and Trademark Office in connection with U.S. Appl. No. 12/182,874, dated Apr. 22, 2013, 11 pages.

(56) References Cited

OTHER PUBLICATIONS

International Preliminary Report on Patentability, issued by the International Bureau of WIPO in connection with International Application No. PCT/US08/058264, dated Sep. 29, 2009, 1 page.
International Search Report, issued by the International Searching Authority in connection with International Application No. PCT/US08/058264, dated Aug. 1, 2008, 2 pages.
Written Opinion, issued by the International Searching Authority in connection with International Application No. PCT/US08/058264, dated Aug. 1, 2008, 5 pages.
International Preliminary Report on Patentability, issued by the International Bureau of WIPO in connection with International Application No. PCT/US08/062273, dated Nov. 3, 2009, 1 page.
International Search Report, issued by the International Searching Authority in connection with International Application No. PCT/US08/062273, dated Sep. 5, 2008, 2 pages.
Written Opinion, issued by the International Searching Authority in connection with International Application No. PCT/US08/062273, dated Sep. 5, 2008, 4 pages.
International Search Report, issued by the International Bureau in connection with International Application No. PCT/US08/062275, dated Sep. 22, 2008, 2 pages.
Written Opinion, issued by the International Bureau in connection with International Application No. PCT/US08/062275, dated Sep. 22, 2008, 6 pages.
International Preliminary Report on Patentability, issued by the International Bureau of WIPO in connection with International Application No. PCT/US08/063984, dated Nov. 17, 2009, 1 page.
International Search Report, issued by the International Bureau in connection with International Application No. PCT/US08/063984, dated Sep. 29, 2008, 3 pages.
Written Opinion, issued by the International Bureau in connection with International Application No. PCT/US08/063984, dated Sep. 29, 2008, 4 pages.
International Preliminary Report on Patentability, issued by the International Bureau of WIPO in connection with International Application No. PCT/US08/063989, dated Nov. 17, 2009, 1 page.
International Search Report, issued by the International Bureau in connection with International Application No. PCT/US08/063989, dated Jul. 17, 2008, 2 pages.
Written Opinion, issued by the International Bureau in connection with International Application No. PCT/US08/063989, dated Jul. 17, 2008, 4 pages.
International Preliminary Report on Patentability, issued by the International Bureau of WIPO in connection with International Application No. PCT/US08/066166, dated Dec. 7, 2009, 1 page.
International Search Report, issued by the International Bureau in connection with International Application No. PCT/US08/066166, dated Aug. 25, 2008, 2 pages.
Written Opinion, issued by the International Bureau in connection with International Application No. PCT/US08/066166, dated Aug. 25, 2008, 6 pages.
International Preliminary Report on Patentability, issued by the International Bureau of WIPO in connection with International Application No. PCT/US08/071639, dated Feb. 2, 2010, 1 page.
Written Opinion, issued by the International Bureau in connection with International Application No. PCT/US08/071639, dated Oct. 22, 2008, 4 pages.
International Preliminary Report on Patentability, issued by the International Bureau of WIPO in connection with International Application No. PCT/US08/074467, dated Mar. 2, 2010, 1 page.
International Search Report, issued by the International Bureau in connection with International Application No. PCT/US08/074467, dated Nov. 17, 2008, 2 pages.
Written Opinion, issued by the International Bureau in connection with International Application No. PCT/US08/074467, dated Nov. 17, 2008, 4 pages.
International Preliminary Report of Patentability, issued by the International Bureau in connection with International Application No. PCT/US10/021535, dated Jul. 26, 2011, 1 page.
International Search Report, issued by the International Bureau in connection with International Application No. PCT/US10/021535, dated Mar. 23, 2010, 3 pages.
Written Opinion, issued by the International Bureau in connection with International Application No. PCT/US10/021535, dated Mar. 23, 2010, 4 pages.
International Preliminary Report of Patentability, issued by the International Bureau in connection with International Application No. PCT/US09/065368, dated Jun. 23, 2011, 2 pages.
International Search Report, issued by the International Bureau in connection with International Application No. PCT/US09/065368, dated Jan. 21, 2010, 3 pages.
Written Opinion, issued by the International Bureau in connection with International Application No. PCT/US09/065368, dated Jan. 21, 2010, 7 pages.
International Preliminary Report on Patentability, issued by the International Bureau of WIPO in connection with International Application No. PCT/US08/062275, dated Nov. 3, 2009, 1 page.
International Search Report, issued by the International Bureau in connection with International Application No. PCT/US08/071639, dated Oct. 22, 2008, 3 pages.
Extended European Search Report, issued by the European Patent Office in connection with European Application No. 08744383.4-2221/2130146, dated Jul. 27, 2011, 6 pages.
Extended European Search Report, issued by the European Patent Office in connection with European Application No. 10173095.0-2221, dated Dec. 17, 2010, 3 pages.
Extended European Search Report, issued by the European Patent Office in connection with European Application No. 10189294.1-2221, dated Mar. 21, 2011, 7 pages.
First Office Action, issued by the State Intellectual Property Office of P.R. China in connection with Patent Application No. 200880104982.1, dated Jan. 25, 2011, 15 pages (includes English translation).
English Translation of First Office Action, issued by the State Intellectual Property Office of P.R. China in connection with Patent Application No. 2008801015007, dated May 25, 2011, 8 pages.
English Translation of First Office Action, issued by the State Intellectual Property Office of P.R. China in connection with Patent Application No. 200880019166.0, dated Jul. 22, 2011, 16 pages.
English Translation of Decision of Rejection, issued by the State Intellectual Property Office of P.R. China in connection with Patent Application No. 200880104982.1, dated Sep. 23, 2011, 10 pages.
Extended European Search Report, issued by the European Patent Office in connection with European Application No. 11006934.1-2221, dated Oct. 25, 2011, 5 pages.
English Translation of First Office Action, issued by the State Intellectual Property Office of P.R. China in connection with Patent Application No. 20080017883.X, dated Nov. 30, 2011, 16 pages.
English Translation of Office Action, issued by the Israel Patent Office in connection with Patent Application No. 203176, dated Feb. 21, 2012, 2 pages.
English Translation of Office Action, issued by the Israel Patent Office in connection with Patent Application No. 203177, dated Mar. 1, 2012, 2 pages.
English Translation of Second Office Action, issued by the State Intellectual Property Office of P.R. China in connection with Patent Application No. 200880101500.7, dated Apr. 5, 2012, 5 pages.
English Translation of Second Office Action, issued by the State Intellectual Property Office of P.R. China in connection with Patent Application No. 200880019166.0, dated Jun. 5, 2012, 8 pages.
English Translation of Second Office Action, issued by the State Intellectual Property Office of P.R. China in connection with Patent Application No. 200880104982.1, dated Jun. 29, 2012, 5 pages.
English Translation of Second Office Action, issued by the State Intellectual Property Office of P.R. China in connection with Patent Application No. 200880017883.X, dated Aug. 10, 2012, 9 pages.
English Translation of Office Action, issued by the Israel Patent Office in connection with Patent Application No. 203176, dated Sep. 27, 2012, 1 page.
English Translation of Office Action, issued by the Israel Patent Office in connection with Patent Application No. 203177, dated Sep. 27, 2012, 1 page.

(56) References Cited

OTHER PUBLICATIONS

Office Action, issued by the Japanese Patent Office in connection with Patent Application No. 2010-501190, dated Oct. 2, 2012, 10 pages (includes English translation).
English Translation of Office Action, issued by the Japanese Patent Office in connection with Patent Application No. 2010-506646, dated Oct. 23, 2012, 3 pages.
English Translation of Third Office Action, issued by the State Intellectual Property Office of P.R. China in connection with Patent Application No. 200880101500.7, dated Nov. 21, 2012, 5 pages.
English Translation of Office Action, issued by the Israeli Patent Office in connection with Patent Application No. 201187, dated Nov. 27, 2012, 2 pages.
Extended European Search Report, issued by the European Patent Office in connection with European Application No. 08796890.5-2319/2170161, dated Dec. 7, 2012, 9 pages.
Notification to Grant Patent Right for Invention, issued by the State Intellectual Property Office of P.R. China in connection with Patent Application No. 200880104982.1, dated Jan. 14, 2013, 4 pages (includes English translation).
Extended European Search Report, issued by the European Patent Office in connection with European Application No. 08770372.4-1265/2152155, dated Feb. 6, 2013, 7 pages.
English Translation of Third Office Action, issued by the State Intellectual Property Office of P.R. China in connection with Patent Application No. 200880017883.X, dated Mar. 18, 2013, 8 pages.
English translation of Notification to Grant Patent Right for Invention, issued by the State Intellectual Property Office of P.R. China in connection with Patent Application No. 200880101500.7, dated Apr. 3, 2013, 2 pages.
Aaker et al., "Warmth in Advertising: Measurement, Impact, and Sequence Effects," Journal of Consumer Research, vol. 12, No. 4, pp. 365-381, (Mar. 1986), 18 pages.
Akam, et al., "Oscillations and Filtering Networks Support Flexible Routing of Information," Neuron, vol. 67, pp. 308-320, Elsevier, (Jul. 29, 2010), 13 pages.
Allen et al., "A Method for Removing Imaging Artifact from Continuous EEG Recorded during Functional MRI," Neuroimage, vol. 12, 230-239, (Aug. 2000), 12 pages.
Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.
Ambler et al., "Ads on the Brain: A Neuro-Imaging Comparison of Cognitive and Affective Advertising Stimuli," London Business School, Centre for Marketing Working Paper, No. 00-902, (Mar. 2000), 23 pages.
Badre, et al. "Frontal Cortex and the Discovery of Abstract Action Rules," Neuron, vol. 66, pp. 315-326, Elsevier, (Apr. 29, 2010), 12 pages.
Bagozzi et al., "The Role of Emotions in Marketing," Journal of the Academy of Marketing Science, vol. 27, No. 2, pp. 184-206, Academy of Marketing Science (1999), 23 pages.
Barcelo, et al., "Prefrontal modulation of visual processing in humans," Nature Neuroscience, vol. 3, No. 4, Nature America, http//neurosci.nature.com, (Apr. 2000), 5 pages.
Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.
Belch et al., "Psychophysiological and cognitive Responses to Sex in Advertising," Advances in Consumer Research, vol. 9, pp. 424-427, (1982), 6 pages.
Bimler et al., "Categorical perception of facial expressions of emotion: Evidence from multidimensional scaling," Cognition and Emotion, vol. 15(5), pp. 633-658 (Sep. 2001), 26 pages.
Blakeslee, "If You Have a 'Buy Button' in Your Brain, What Pushes It?" The New York Times, www.nytimes.com, (Oct. 19, 2004), 3 pages.
Braeutigam, "Neuroeconomics-From neural systems to economic behavior," Brain Research Bulletin, vol. 67, pp. 355-360, Elsevier, (2005), 6 pages.
Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, (2007), 4 pages.
Buschman, et al., "Serial, Covert Shifts of Attention during Visual Search Are Reflected by the Frontal Eye Fields and Correlated with Population Oscillations," Neuron, vol. 63, pp. 386-396, Elsevier, (Aug. 13, 2009), 11 pages.
Canolty, et al., "High Gamma Power Is Phase-Locked to Theta Oscillations in Human Neocortex," Science, vol. 313, www.sciencemag.org, (Sep. 15, 2006), 3 pages.
Cheng, et al. "Gender Differences in the Mu Rhythm of the Human Mirror-Neuron System," PLos ONE, vol. 3, Issue 5, www.plosone.org, (May 2008), 7 pages.
Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, (Mar. 28, 2007), 8 pages.
Clifford, "Billboards That Look Back," The New York Times, NYTimes.com, available at http://www.nytimes.com/2008/05/31/business/media/31billboard.html, (May 31, 2008), 4 pages.
Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.
Davidson, et al., "The functional neuroanatomy of emotion and affective style," TRENDS in Cognitive Sciences, vol. 3, No. 1, (Jan. 1999), 11 pages.
De Gelder et al., "Categorical Perception of Facial Expressions: Categories and their Internal Structure," Cognition and Emotion, vol. 11(1), pp. 1-23 (1997), 23 pages.
D'Esposito, "From cognitive to neural models of working memory," Phil. Trans. R. Soc. B, doi: 10.1098/rstb.2007.2086, (Mar. 30, 2007), 12 pages.
Desmet, "Measuring Emotions: Development and Application of an Instrument to Measure Emotional Responses to Products," to be published in Funology: From Usability to Enjoyment, pp. 1-13, Kluwer Academic Publishers, (Blythe et al., eds., 2004), 13 pages.
Dien, et al., "Application of Repeated Measures ANOVA to High-Density ERP Datasets: A Review and Tutorial," in Event-Related Potentials: A Methods Handbook pp. 57-82, (Todd C. Handy, ed., 2005), 14 pages.
Edgar, et al., "Digital Filters in ERP Research," in Event-Related Potentials: A Methods Handbook pp. 85-113, (Todd C. Handy, ed., 2005), 15 pages.
EEG Protocols, "Protocols for EEG Recording," retrieved from the Internet on Aug. 23, 2011, http://www.q-metrx.com/EEGrecordingProtocols.pdf, (Nov. 13, 2007), 3 pages.
Engel et al., "Dynamic Predictions: Oscillations and Synchrony in Top-down Processing," Nature Reviews: Neuroscience, vol. 2, pp. 704-716, Macmillian Magazines Ltd., (Oct. 2001), 13 pages.
Filler, "MR Neurography and Diffusion Tensor Imaging: Origins, History & Clinical Impact of the first 50,000 Cases With an Assessment of Efficacy and Utility in a Prospective 5,000 Patent Study Group," Institute for Nerve Medicine, (Nov. 7, 2008), 56 pages.
Flinker, A. et al, "Sub-centimeter language organization in the human temporal lobe," Brain and Language, Elsevier Inc., (2010), doi.org/10.1016/j.bandl.2010.09.009, 7 pages.
Fogelson, et al., "Prefrontal cortex is critical for contextual processing: evidence from brain lesions," Brain: A Journal of Neurology, vol. 132, pp. 3002-3010, doi:10.1093/brain/awp230, (Aug. 27, 2009), 9 pages.
Friedman, et al., "Event-Related Potential (ERP) Studies of Memory Encoding and Retrieval: A Selective Review," Microscopy Research and Technique 51:6-22, Wiley-Liss, Inc. (2000), 23 pages.

(56) References Cited

OTHER PUBLICATIONS

Fries, "A mechanism for cognitive dynamics: neuronal communication through neuronal coherence," Trends in Cognitive Sciences, vol. 9, No. 10, pp. 474-480, Elsevier B.V. www.sciencedirect.com, (Oct. 2005), 7 pages.
Fuster, "Cortex and Memory: Emergence of a New Paradigm," Journal of Cognitive Neuroscience, vol. 21, No. 11, pp. 2047-2072, Massachusetts Institute of Technology, (Nov. 2009), 26 pages.
Gaillard, "Problems and Paradigms in ERP Research," Biological Psychology, Elsevier Science Publisher B.V. (1988), 10 pages.
Gargiulo et al., "A Mobile EEG System With Dry Electrodes," (Nov. 2008), 4 pages.
Gazzaley et al., "Top-down Enhancement and Suppression of Magnitude and Speed of Neural Activity," Journal of Cognitive Neuroscience, vol. 17, No. 3, pp. 507-517, Massachusetts Institute of Technology, (2005), 11 pages.
Griss et al., "Characterization of micromachined spiked biopotential electrodes", Biomedical Engineering, IEEE Transactions (Jun. 2002), 8 pages.
Haq, "This Is Your Brain on Advertising," BusinessWeek, Market Research, (Oct. 8, 2007), 4 pages.
Hartikainen et al., Manuscript Draft of "Emotionally arousing stimuli compete with attention to left hemispace," NeuroReport, (Sep. 8, 2007), 26 pages.
Hazlett, et al., "Emotional Response to Television Commercials: Facial EMG vs. Self-Report," Journal of Advertising Research, (Apr. 1999), 17 pages.
Herrmann, et al., "Mechanisms of human attention: event-related potentials and oscillations," Neuroscience and Biobehavioral Reviews, pp. 465-476, Elsevier Science Ltd., www.elsvevier.com/locate/neubiorev, (2001), 12 pages.
Hopf, et al., "Neural Sources of Focused Attention in Visual Search," Cerebral Cortex, 10:1233-1241, Oxford University Press, (Dec. 2000), 9 pages.
Jung et al., "Analysis and Visualization of Single-Trial Event-Related Potentials," Human Brain Mapping vol. 14, 166-185 (2001), 20 pages.
Kay et al., "Identifying natural images from human brain activity," Nature, vol. 452, pp. 352-356, Nature Publishing Group, (Mar. 20, 2008), 5 pages.
Keren, et al., "Saccadic spike potentials in gamma-band EEG: Characterization, detection and suppression," NeuroImage, http://dx.doi:10.1016/j.neuroimage.2009.10.057, (Oct. 2009), 16 pages.
Kishiyama, et al., "Novelty Enhancements in Memory Are Dependent on Lateral Prefrontal Cortex," The Journal of Neuroscience, pp. 8114-8118, Society for Neuroscience (Jun. 24, 2009), 5 pages.
Kishiyama, et al., "Socioeconomic Disparities Affect Prefrontal Function in Children," Journal of Cognitive Neuroscience pp. 1106-1115, Massachusetts Institute of Technology, (2008), 10 pages.
Klimesch, "EEG alpha and theta oscillations reflect cognitive and memory performance a review and analysis," Brain Research Reviews, vol. 29, 169-195, (1999), 27 pages.
Knight, "Contribution of human hippocampal region to novelty detection," Nature, vol. 383, www.nature.com, (Sep. 19, 1996), 4 pages.
Knight, "Consciousness Unchained: Ethical Issues and the Vegetative and minimally Conscious State," The American Journal of Bioethics, 8:9, 1-2, http://dx.doi.org/10.1080/15265160802414524, (Sep. 1, 2008), 3 pages.
Knight, et al., "Prefrontal cortex regulates inhibition and excitation in distributed neural networks," Acta Psychologica vol. 101, pp. 159-178, Elsevier (1999), 20 pages.
Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., (1984), 12 pages.
Krakow et al., "Methodology: EEG-correlated fMRI," Functional Imaging in the Epilepsies, (Lippincott Williams & Wilkins, 2000), 17 pages.
Krugman, "Brain Wave Measures of Media Involvement," Journal of Advertising Research vol. 11, 3-9 (Feb. 1971), 7 pages.
Lachaux et al., "Measuring Phase Synchrony in Brain Signals," Human Brain Mapping 8 (1999), 194-208, 15 pages.
Lee et al., "What is 'neuromarketing'? A discussion and agenda for future research," International Journal of Psychophysiology, vol. 63, pp. 199-204, Elsevier (2006), 6 pages.
Lekakos, "Personalized Advertising Services Through Hybrid Recommendation Methods: The Case of Digital Interactive Television," Department of Informatics, Cyprus University, (2004), 11 pages.
Lewis et al., "Market Researchers make Increasing use of Brain Imaging," ACNR, vol. 5, No. 3, pp. 36-37, (Jul./Aug. 2005), 2 pages.
Luck, et al., "The speed of visual attention in schizophrenia: Electrophysiological and behavioral evidence," Schizophrenia Research, pp. 174-195, Elsevier B.V. www.sciencedirect.com, (2006), 22 pages.
Lui et al., "Marketing Strategies in Virtual Worlds," The Data Base for Advances in Information Systems, vol. 38, No. 4, pp. 77-80, (Nov. 2007), 4 pages.
Makeig, et al., "Mining event-related brain dynamics," TRENDS in Cognitive Sciences, vol. 8, No. 5, (May 2004), www.sciencedirect.com, 7 pages.
Makeig, et al., "Dynamic Brain Sources of Visual Evoked Responses," Science, vol. 295, www.sciencemag.org, (Jan. 25, 2002), 5 pages.
The Mathworks, Inc., "MATLAB Data Analysis: Version 7," p. 4-19 (2005), 3 pages.
Merriam-Webster Online Dictionary definition for "tangible," available at http://www.merriam-webster.com/dictionary/tangible, 1 page.
Merriam Webster Online Dictionary, Definition of Virtual Reality, available at http://www.merriam-webster.com/dictionary/virtual%20reality, 2 page.
Miltner, et al., "Coherence of gamma-band EEG activity as a basis for associative learning," Nature, vol. 397, www.nature.com, (Feb. 4, 1999), 3 pages.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.
Neurofocus—Neuroscientific Analysis for Audience Engagement, accessed on Jan. 8, 2010 at http://web.archive.org/web/20080621114525/www.neurofocus.com /BrandImage.htm, (2008), 2 pages.
Newell et al., "Categorical perception of familiar objects," Cognition, vol. 85, Issue 2, pp. 113-143 (Sep. 2002), 31 pages.
Nielsen, "Neuroinformatics in Functional Neuroimaging," Informatics and Mathematical Modeling, Technical University of Denmark, (Aug. 30, 2002), 241 pages.
Oberman et al., "EEG evidence for mirror neuron activity during the observation of human and robot actions: Toward an analysis of the human qualities of interactive robots," Neurocomputing 70 (2007) 2194-2203, 10 pages.
Osborne, "Embedded Watermarking for image Verification in Telemedicine," Thesis submitted for the degree of Doctor of Philosophy, Electrical and Electronic Engineering, University of Adelaide (2005), 219 pages.
Padgett et al., "Categorical Perception in Facial Emotion Classification," In Proceedings of the 18th Annual Conference of the Cognitive Science Society, pp. 249-253 (1996), 5 pages.
Page et al., "Cognitive Neuroscience, Marketing and Research," Congress 2006—Foresight—The Predictive Power of Research Conference Papers, ESOMAR Publications, (Sep. 17, 2006), 25 pages.
Paller, et al., "Validating neural correlates of familiarity," TRENDS in Cognitive Sciences, vol. 11, No. 6, www.sciencedirect.com, (May 2, 2007), 8 pages.
Palva et al., "Phase Synchrony Among Neuronal Oscillations in the Human Cortex," Journal of Neuroscience 25 (2005), 3962-3972, 11 pages.
Picton, et al., "Guidelines for using human event-related potentials to study cognition: Recording standards and publication criteria," Psychophysiology, pp. 127-152, Society for Psychophysiological Research, (2000), 26 pages.

(56) References Cited

OTHER PUBLICATIONS

Rizzolatti et al., "The Mirror-Neuron System," Annu. Rev. Neurosci., vol. 27, pp. 169-192, (Mar. 5, 2004), 30 pages.
Ruchkin et al., "Modality-specific processing streams in verbal working memory: evidence from spatio-temporal patterns of brain activity," Cognitive Brain Research, vol. 6, pp. 95-113, Elsevier, (1997), 19 pages.
Rugg, et al., "Event-related potentials and recognition memory," TRENDS in Cognitive Sciences, vol. 11, No. 6, www.sciencedirect.com, (May 3, 2007), 7 pages.
Rugg, et al., "The ERP and cognitive psychology: conceptual issues," (Sep. 1996), 7 pages.
"User monitoring," Sapien Systems, available at http://web.archive.org/web/20030818043339/http:/www.sapiensystems.com/eyetracking.html, (Aug. 18, 2003), 1 page.
Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.
Spencer, "Averaging, Detection, and Classification of Single-Trial ERPs," in Event-Related Potentials: A Methods Handbook, pp. 209-227, (Todd C. Handy, ed., 2005), 10 pages.
Arousal in Sport, in Encyclopedia of Applied Psychology, vol. 1, p. 159, retrieved from Google Books, (Spielberger, ed., Elsevier Academic Press, 2004), 1 page.
Srinivasan, "High-Resolution EEG: Theory and Practice," in Event-Related Potentials: A Methods Handbook, pp. 167-188, (Todd C. Handy, ed., 2005), 12 pages.
Sullivan et al., "A brain-machine interface using dry-contact, low-noise EEG sensors," In Proceedings of the 2008 IEEE International Symposium on Circuits and Systems, (May 18, 2008), 4 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.
Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.
Taheri, et al., "A dry electrode for EEG recording," Electroencephalography and clinical Neurophysiology, pp. 376-383, Elsevier Science Ireland Ltd. (1994), 8 pages.
Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.
Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.
Voytek, et al., "Prefrontal cortex and basal ganglia contributions to visual working memory," PNAS Early Edition, www.pnas.org/cgi/doi/10.1073/pnas.1007277107, (2010), 6 pages.
Voytek, et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, (Nov. 2009) 12 pages.
Wang, "Neurophysiological and Computational Principles of Cortical Rhythms in Cognition," Physiol Rev 90: pp. 1195-1268, American Physiological Society, www.prv.org, (2010), 75 pages.
"Functional magnetic resonance imaging," retrieved online from Wikipedia, the Free Encyclopedia on Aug. 23, 2011, at http://en.wikipedia.org/w/index.php?title=Functional_magnetic_resonance_imaging&oldid=319601772, (Oct. 13, 2009), 8 pages.
William, "Brain Signals to Control Movement of Computer Cursor," Blog article: Brain Signals to Control Movement of Computer Cursor, Artificial Intelligence, retrieved from the Internet on Aug. 17, 2011, http://whatisartificialintelligence.com/899/brain-signals-to-control-movement-of-computer-cursor/, (Feb. 17, 2010), 3 pages.
Woldorf, "Distortion of ERP averages due to overlap from temporally adjacent ERPs: Analysis and correction," Psychophysiology, Society for Psychophysiological Research, Cambridge University Press (1993), 22 pages.
Woodman, et al., "Serial Deployment of Attention During Visual Search," Journal of Experimental Psychology: Human Perception and Performance, vol. 29, No. 1, pp. 121-138, American Physiological Association (2003), 18 pages.
Yamaguchi, et al., "Rapid-Prefrontal—Hippocampal Habituation to Novel Events," The Journal of Neuroscience, pp. 5356-5363, Society for Neuroscience, (Apr. 29, 2004), 8 pages.
Yap et al., "TIMER: Tensor Image Morphing for Elastic Registration," Neuroimage, vol. 47, (May 3, 2009), 15 pages.
Yuval-Greenberg, et al., "Transient Induced Gamma-Bands Response in EEG as a Manifestation of Miniature Saccades," Neuron, vol. 58, pp. 429-441, Elsevier Inc. (May 8, 2008), 13 pages.
Ziegenfuss, "Neuromarketing: Advertising Ethical & Medical Technology," The Brownstone Journal, vol. XII, Boston University, pp. 69-73, (May 2005), 5 pages.
Zyga, "A Baseball Cap That Can Read Your Mind," PhysOrg.com, located at www.physorg.com/news130152277.html, (May 16, 2008), 11 pages.
Non-Final Office Action, issued by the United States Patent and Trademark Office in connection with U.S. Appl. No. 12/546,586, dated Apr. 25, 2013, 34 pages.
Non-Final Office Action, issued by the United States Patent and Trademark Office in connection with U.S. Appl. No. 13/444,149, dated May 2, 2013, 27 pages.
Notice of Allowance, issued by the United States Patent and Trademark Office in connection with U.S. Appl. No. 12/056,190, dated May 8, 2013, 4 pages.
Notice of Allowance, issued by the United States Patent and Trademark Office in connection with U.S. Appl. No. 12/056,211, dated May 8, 2013, 5 pages.
Notice of Allowance, issued by the United States Patent and Trademark Office in connection with U.S. Appl. No. 12/135,074, dated May 8, 2013, 5 pages.
Notice of Allowance, issued by the United States Patent and Trademark Office in connection with U.S. Appl. No. 12/199,596, dated May 8, 2013, 7 pages.
Notice of Allowance, issued by the United States Patent and Trademark Office in connection with U.S. Appl. No. 13/569,711, dated May 14, 2013, 6 pages.
Notice of Allowance, issued by the United States Patent and Trademark Office in connection with U.S. Appl. No. 12/182,874, dated May 17, 2013, 6 pages.
Final Office Action, issued by the United States Patent and Trademark Office in connection with U.S. Appl. No. 12/778,828, dated May 23, 2013, 25 pages.
Office Communication to Applicant, issued by the United States Patent and Trademark Office in connection with U.S. Appl. No. 12/234,388, dated May 24, 2013, 2 pages.
Non-Final Office Action, issued by the United States Patent and Trademark Office in connection with U.S. Appl. No. 12/884,034, dated May 28, 2013, 12 pages.
Notice of Allowance, issued by the United States Patent and Trademark Office in connection with U.S. Appl. No. 12/135,074, dated May 31, 2013, 5 pages.
Notice of Allowance, issued by the United States Patent and Trademark Office in connection with U.S. Appl. No. 12/056,211, dated Jun. 3, 2013, 5 pages.
Notice of Allowance, issued by the United States Patent and Trademark Office in connection with U.S. Appl. No. 12/199,596, dated Jun. 3, 2013, 5 pages.
Notice of Allowance, issued by the United States Patent and Trademark Office in connection with U.S. Appl. No. 12/199,596, dated Jun. 11, 2013, 7 pages.
Notice of Allowance, issued by the United States Patent and Trademark Office in connection with U.S. Appl. No. 12/545,455, dated Jun. 11, 2013, 9 pages.
Notice of Allowance, issued by the United States Patent and Trademark Office in connection with U.S. Appl. No. 12/056,190, dated Jun. 13, 2013, 5 pages.

(56) References Cited

OTHER PUBLICATIONS

Office Communication to Applicant, issued by the United States Patent and Trademark Office in connection with U.S. Appl. No. 12/234,388, dated Jun. 13, 2013, 2 pages.
Notice of Allowance, issued by the United States Patent and Trademark Office in connection with U.S. Appl. No. 12/135,074, dated Jun. 21, 2013, 5 pages.
Non-Final Office Action, issued by the United States Patent and Trademark Office in connection with U.S. Appl. No. 13/105,774, dated Jun. 26, 2013, 10 pages.
English Translation of Office Action, issued by the Israeli Patent Office in connection with Patent Application No. 203176, dated Apr. 23, 2013, 1 page.
English Translation of Notice Prior to Allowance, issued by the Israeli Patent Office in connection with Patent Application No. 203176, dated Jun. 30, 2013, 1 page.
Merriam-Webster Online Dictionary, Definition for "Resonance," available at http://www.merriam-webster.com/dictionary/resonance, 4 pages.
Enghoff, Sigurd, Thesis: "Moving ICA and Time-Frequency Analysis in Event-Related EEG Studies of Selective Attention," Technical University of Denmark, (Dec. 1999), 54 pages.
Zhang, P., "Will You Use Animation on Your Web Pages?" Doing Business on the Internet: Opportunities and Pitfalls, C. Romm and F. Sudweeks (eds.), Spring-Verlag (1999), 17 pages.
Notice of Allowance, issued by the United States Patent and Trademark Office in connection with U.S. Appl. No. 12/182,874, dated Jul. 29, 2013, 6 pages.
Office Action, issued by the United States Patent and Trademark Office in connection with U.S. Appl. No. 12/546,586, dated Sep. 12, 2013, 13 pages.
Notice of Allowance, issued by the United States Patent and Trademark Office in connection with U.S. Appl. No. 12/199,596, dated Sep. 13, 2013, 7 pages.
Office Action, issued by the United States Patent and Trademark Office in connection with U.S. Appl. No. 12/113,870, dated Sep. 17, 2013, 11 pages.
Notice of Allowance, issued by the United States Patent and Trademark Office in connection with U.S. Application No. 12/778,828, dated Oct. 8, 2013, 11 pages.
English Translation of Office Action, issued by the Japanese Patent Office in connection with Patent Application No. 2010-523112, dated Jul. 30, 2013, 2 pages.
Decision to Grant Patent, issued by the Japanese Patent Office in connection with Patent Application No. 2010-506646, dated Aug. 6, 2013, 4 pages (includes English translation).
English Translation of Decision on Rejection, issued by the Chinese Patent Office in connection with Patent Application No. 200880017883.X, dated Aug. 5, 2013, 13 pages.
Final Office Action, issued by the United States Patent and Trademark Office in connection with U.S. Appl. No. 12/884,034, dated Oct. 23, 2013, 17 pages.
Notice of Allowance, issued by the United States Patent and Trademark Office in connection with U.S. Appl. No. 12/199,596, dated Nov. 6, 2013, 7 pages.
Final Office Action, issued by the United States Patent and Trademark Office in connection with U.S. Appl. No. 13/444,149, dated Nov. 19, 2013, 11 pages.
Non-Final Office Action, issued by the United States Patent and Trademark Office in connection with U.S. Appl. No. 12/122,253, dated Dec. 3, 2013, 16 pages.
Notice of Allowance, issued by the United States Patent and Trademark Office in connection with U.S. Appl. No. 12/199,596, dated Dec. 23, 2013, 7 pages.
Final Office Action, issued by the United States Patent and Trademark Office in connection with U.S. Appl. No. 13/105,774, dated Jan. 16, 2014, 11 pages.
English Translation of Office Action, issued by the Japanese Patent Office in connection with Patent Application No. 2010-520159, dated Oct. 1, 2013, 2 pages.
Extended European Search Report, issued by the European Patent Office in connection with European Application No. 08798799.6-1657/2180825, dated Nov. 4, 2013, 9 pages.
Coan et al., "Voluntary Facial Expression and Hemispheric Asymmetry Over the Frontal Cortex," Psycophysiology (Nov. 2001), 912-924, 14 pages.
Duchowski, "A Breadth-First Survey of Eye-tracking Applications," Beahavior Research Methods, Instruments, and Computers (Nov. 2002), 455-470, 16 pages.
Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.
Rothschild et al., "Predicting Memory for Components of TV Commercials from EEG," Journal of Consumer Research (Mar. 1990), p. 472-478, 8 pages.
Beaver, John D., et al., "Individual Differences in Reward Drive Predict Neural Responses to Images of Food", J. of Neuroscience, (May 10, 2006), 5160-5166, 7 pages.
Tapert, Susan F., et al., "Neural Response to Alcohol Stimuli in Adolescents With Alcohol Use Disorder", Arch Gen Psychiatry (Jul. 2003), 727-735, 9 pages.
Shandlen, Michael N. et al., "A Computational Analysis of the Relationship between Neuronal and Behavioral Responses to Visual Motion", The Journal of Neuroscience, (Feb. 15, 1996) 1486-1510, 25 pages.
Office Action, issued by the United States Patent and Trademark Office in connection with U.S. Appl. No. 13/730,541, dated Jan. 30, 2014, 12 pages.
Office Action, issued by the United States Patent and Trademark Office in connection with U.S. Appl. No. 13/730,550, dated Jan. 31, 2014, 5 pages.
Office Action, issued by the United States Patent and Trademark Office in connection with U.S. Appl. No. 13/965,805, dated Feb. 3, 2014, 15 pages.
Notice of Allowance, issued by the United States Patent and Trademark Office in connection with U.S. Appl. No. 13/444,149, dated Feb. 3, 2014, 5 pages.
Office Action, issued by the United States Patent and Trademark Office in connection with U.S. Appl. No. 12/113,870, dated Feb. 4, 2014, 12 pages.
Office Action, issued by the United States Patent and Trademark Office in connection with U.S. Appl. No. 12/546,586, dated Feb. 6, 2014, 17 pages.
Office Action, issued by the United States Patent and Trademark Office in connection with U.S. Appl. No. 13/730,564, dated Feb. 10, 2014, 14 pages.
Office Action, issued by the United States Patent and Trademark Office in connection with U.S. Appl. No. 12/884,034, dated Feb. 10, 2014, 18 pages.
Mehta, A. et al., "Reconsidering Recall and Emotion in Advertising", Journal of Advertising Research, (Mar. 2006), 49-56, 9 pages.
Cheung, Kwok-Wai, et al., "Mining Customer Product Ratings for Personalized Marketing," Decision Support Systems 35 (2003) 231-243, 13 pages.
English Translation of Office Action, issued by the Israel Patent Office in connection with Patent Application No. 201187, dated Apr. 2, 2013, 2 pages.
Notice of Allowance, issued by the United States Patent and Trademark Office in connection with U.S. Appl. No. 13/730,550, dated May 27, 2014, 8 pages.
Office Action, issued by the United States Patent and Trademark Office in connection with U.S. Appl. No. 12/608,660, dated Jun. 2, 2014, 13 pages.
Office Action, issued by the United States Patent and Trademark Office in connection with U.S. Appl. No. 12/122,253, dated Jun. 5, 2014, 25 pages.
Final Office Action, issued by the United States Patent and Trademark Office in connection with U.S. Appl. No. 12/113,870, dated Jul. 1, 2014, 16 pages.
Decision to Grant Patent, issued by the Japanese Patent Office in connection with Patent Application No. 2010-523112, dated Apr. 8, 2014, 4 pages (includes English translation).

(56) References Cited

OTHER PUBLICATIONS

Darrow, Chester, "Psychological and psychophysiological significance of the electroencephalogram," Psychological Review (May 1947) 157-168, 12 pages.
Stamm, John, "On the Relationship between Reaction Time to Light and Latency of Blocking the Alpha Rhythm," Electroencephalography and Clinical Neurophysiology (Feb. 1952), 61-68, 8 pages.
Mizuki, Yashushi, et al., "Periodic Appearance of the Theta Rhythm in the Frontal Midline Area During Performance of a Mental Task,:" Electroencephalography and Clinical Neurophysiology (Aug. 1980), 345-351, 7 pages.
Decision to Grant Patent, issued by the Korean Patent Office in connection with Patent Application No. 10-2009-7022551, dated Aug. 13, 2014, 3 pages (includes English translation).
Non-Final Office Action, issued by the United States Patent and Trademark Office in connection with U.S. Appl. No. 13/730,541, dated Jul. 23, 2014, 13 pages.
Non-Final Office Action, issued by the United States Patent and Trademark Office in connection with U.S. Appl. No. 13/965,805, dated Aug. 6, 2014, 18 pages.
Non-Final Office Action, issued by the United States Patent and Trademark Office in connection with U.S. Appl. No. 13/730,550, dated Aug. 14, 2014, 4 pages.
Non-Final Office Action, issued by the United States Patent and Trademark Office in connection with U.S. Appl. No. 13/730,564, dated Aug. 15, 2014, 15 pages.
Non-Final Office Action, issued by the United States Patent and Trademark Office in connection with U.S. Appl. No. 12/884,034, dated Aug. 21, 2014, 20 pages.
Non-Final Office Action, issued by the United States Patent and Trademark Office in connection with U.S. Appl. No. 12/608,685, dated Sep. 4, 2014, 16 pages.
Non-Final Office Action, issued by the United States Patent and Trademark Office in connection with U.S. Appl. No. 13/105,774, dated Sep. 18, 2014, 14 pages.
Final Office Action, issued by the United States Patent and Trademark Office in connection with U.S. Appl. No. 12/546,586, dated Sep. 29, 2014, 21 pages.
Ekman, P. Friesen, W., Measuring Facial Movement, Environmental Psychology and Nonverbal Behavior, 1 (1) (Fall 1976), pp. 56-75, 20 pages.
Ekman, P. Friesen, W.V., *Facial Action Coding System: A Technique for Measurement of Facial Movement*, Consulting Psychologists Press, Palo Alto, Calif. (1978). (Book, copy not provided.).
Ekman, P. Friesen, W., *Unmasking the Face—A Guide to Recognizing Emotions from Facial Clues*, Prentice-Hall, Inc., Englewood Cliffs, N.J. (1979). (Book, copy not provided.).
Ekman, P. Friesen, W., Ancoli, S., Facial Signs of Emotional Experience, J. Personality & Social Psychology, 39(6) (Dec. 1980), pp. 1125-1134, 10 pages.
Izard, C. E., *The Maximally Discriminative Facial Movement Coding System*, (Rev. ed.), Instructional Resources Center, University of Delaware, Newark, Del. (1983). (Book, copy not provided.).
Izard, C., Dougherty, L., Hembree, E., *A System for Identifying Affect Expressions by Holistic Judgments* (*AFFEX*), Instructional Resources Center, University of Delaware, Newark, Del. (1983). (Book, copy not provided).
Jia, X., Nixon, M.S., Extending the Feature Set for Automatic Face Recognition, International Conference on Image Processing and Its Applications (Apr. 7-9, 1992), 6 pages.
Lisetti, C., Nasoz, F., Using Noninvasive Wearable Computers to Recognize Human Emotions from Physiological Signals, EURASIP J. Applied Signal Processing, 11 (Sep. 2004), pp. 1672-1687, 16 pages.
Non-Final Office Action, issued by the United States Patent and Trademark Office in connection with U.S. Appl. No. 14/177,698, dated Oct. 24, 2014, 13 pages.
Advisory Action, issued by the United States Patent and Trademark Office in connection with U.S. Appl. No. 12/546,586, dated Dec. 22, 2014, 3 pages.
English Translation of Notification of Provisional Rejection, issued by the Korean Patent Office in connection with Patent Application No. 10-2010-7001406, dated Oct. 21, 2014, 1 page.
Non-Final Office Action, issued by the United States Patent and Trademark Office in connection with U.S. Appl. No. 13/730,550, dated Feb. 20, 2015, 12 pages.
Final Office Action, issued by the United States Patent and Trademark Office in connection with U.S. Appl. No. 12/608,660, dated Feb. 20, 2015, 52 pages.
Final Office Action, issued by the United States Patent and Trademark Office in connection with U.S. Appl. No. 13/965,805, dated Mar. 6, 2015, 18 pages.
Non-Final Office Action, issued by the United States Patent and Trademark Office in connection with U.S. Appl. No. 13/708,344, dated Apr. 9, 2015, 12 pages.
Final Office Action, issued by the United States Patent and Trademark Office in connection with U.S. Appl. No. 14/177,698, dated Apr. 24, 2015, 13 pages.
Final Office Action, issued by the United States Patent and Trademark Office in connection with U.S. Appl. No. 12/608,685, dated May 5, 2015, 7 pages.
Final Office Action, issued by the United States Patent and Trademark Office in connection with U.S. Appl. No. 13/105,774, dated May 14, 2015, 15 pages.
Final Office Action, issued by the United States Patent and Trademark Office in connection with U.S. Appl. No. 12/884,034, dated May 14, 2015, 22 pages.
Final Office Action, issued by the United States Patent and Trademark Office in connection with U.S. Appl. No. 13/730,564, dated May 22, 2015, 6 pages.
Final Office Action, issued by the United States Patent and Trademark Office in connection with U.S. Appl. No. 13/249,512, dated Jun. 30, 2015, 36 pages.
Notification of Provisional Rejection, issued by the Korean Patent Office in connection with Patent Application No. 10-2010-7001406, dated Jun. 24, 2015, 9 pages (includes partial translation).
McClure, Samuel, et al., "Neural Correlates of Behavioral Preference for Culturally Familiar Drinks," Neuron (Oct. 14, 2004), 379-387, 9 pages.
English Translation of Office Action, issued by the Israel Patent Office in connection with Patent Application No. 201187, dated Jun. 22, 2015, 4 pages.
Examiner's Answer, issued by the United States Patent and Trademark Office in connection with U.S. Appl. No. 12/113,870, dated Jul. 30, 2015, 14 pages.
Examiner's Answer, issued by the United States Patent and Trademark Office in connection with U.S. Appl. No. 12/122,253, dated Aug. 4, 2015, 29 pages.
Non-Final Office Action, issued by the United States Patent and Trademark Office in connection with U.S. Appl. No. 14/177,698, dated Aug. 19, 2015, 12 pages.
Examiner's Answer, issued by the United States Patent and Trademark Office in connection with U.S. Appl. No. 12/546,586, dated Sep. 11, 2015, 7 pages.
Final Office Action, issued by the United States Patent and Trademark Office in connection with U.S. Appl. No. 13/730,550, dated Sep. 2, 2015, 6 pages.
Non-Final Office Action, issued by the United States Patent and Trademark Office in connection with U.S. Appl. No. 12/410,380, dated Sep. 10, 2015, 15 pages.
Advisory Action, issued by the United States Patent and Trademark Office in connection with U.S. Appl. No. 12/884,034, dated Sep. 16, 2015, 3 pages.
Non-Final Office Action, issued by the United States Patent and Trademark Office in connection with U.S. Appl. No. 13/705,525, dated Sep. 30, 2015, 12 pages.
Non-Final Office Action, issued by the United States Patent and Trademark Office in connection with U.S. Appl. No. 13/965,805, dated Sep. 30, 2015, 6 pages.
Final Office Action, issued by the United States Patent and Trademark Office in connection with U.S. Appl. No. 13/708,344, dated Nov. 20, 2015, 28 pages.

(56) References Cited

OTHER PUBLICATIONS

Translation of Reexamination Decision, issued by the Chinese Patent Office in connection with Patent Application No. 200880017883.X, dated Nov. 13, 2015, 1 page.
Non-Final Office Action, issued by the United States Patent and Trademark Office in connection with U.S. Appl. No. 12/608,685, dated Dec. 17, 2015, 14 pages.
Examiner's Answer, issued by the United States Patent and Trademark Office in connection with U.S. Appl. No. 13/730,541, dated Dec. 18, 2015, 7 pages.
Notice of Allowance, issued by the United States Patent and Trademark Office in connection with U.S. Appl. No. 14/177,698, dated Jan. 14, 2016, 36 pages.
Non-Final Office Action, issued by the United States Patent and Trademark Office in connection with U.S. Appl. No. 12/608,660, dated Jan. 22, 2016, 38 pages.
Final Office Action, issued by the United States Patent and Trademark Office in connection with U.S. Appl. No. 13/708,525, dated Feb. 3, 2016, 22 pages.
Non-Final Office Action, issued by the United States Patent and Trademark Office in connection with U.S. Appl. No. 12/410,372, dated Feb. 23, 2016, 24 pages.
English Translation of Notification of Provisional Rejection, issued by the Korean Patent Office in connection with Patent Application No. 10-2010-7001406, dated Jan. 26, 2016, 1 page.
English Translation of Notification to Grant Patent Right for Invention, issued by the State Intellectual Property Office of P.R. China in connection with Patent Application No. 200880017883.X, dated Feb. 3, 2016, 2 pages.
Final Office Action, issued by the United States Patent and Trademark Office in connection with U.S. Appl. No. 12/410,380, dated Mar. 22, 2016, 27 pages.
Final Office Action, issued by the United States Patent and Trademark Office in connection with U.S. Appl. No. 12/608,685, dated Mar. 30, 2016, 23 pages.
Advisory Action, issued by the United States Patent and Trademark Office in connection with U.S. Appl. No. 13/708,525, dated Apr. 6, 2016, 3 pages.
Examiner's Answer, issued by the United States Patent and Trademark Office in connection with U.S. Appl. No. 13/730,564, dated Apr. 8, 2016, 7 pages.
Final Office Action, issued by the United States Patent and Trademark Office in connection with U.S. Appl. No. 13/965,805, dated Apr. 21, 2016, 33 pages.
Final Office Action, issued by the United States Patent and Trademark Office in connection with U.S. Appl. No. 12/234,372, dated May 12, 2016, 61 pages.
Non-Final Office Action, issued by the United States Patent and Trademark Office in connection with U.S. Appl. No. 12/884,034, dated May 20, 2016, 69 pages.
Non-Final Office Action, issued by the United States Patent and Trademark Office in connection with U.S. Appl. No. 13/945,357, dated May 20, 2016, 22 pages.
M. Corbetta et al., "Control of Goal-Directed and Stimulus-Driven Attention in the Brain," Nature Reviews Neuroscience, vol. 3, pp. 201-215 (Mar. 2002), 15 pages.
Becker, "A Study of Web Usability for Older Adults Seeking Online Health Resources," ACM Transactions on Computer-Human Interaction, vol. 11, No. 4, pp. 387-406 (Dec. 2004), 20 pages.
Non-Final Office Action, issued by the United States Patent and Trademark Office in connection with U.S. Appl. No. 12/410,380, dated Jun. 17, 2016, 20 pages.
Notice of Allowance, issued by the United States Patent and Trademark Office in connection with U.S. Appl. No. 12/608,660, dated Jul. 29, 2016, 67 pages.
Examiner's Answer, issued by the United States Patent and Trademark Office in connection with U.S. Appl. No. 13/730,550, dated Jul. 27, 2016, 20 pages.
Advisory Action, issued by the United States Patent and Trademark Office in connection with U.S. Appl. No. 12/234,372, dated Aug. 8, 2016, 3 pages.
Non-Final Office Action, issued by the United States Patent and Trademark Office in connection with U.S. Appl. No. 12/413,297, dated Aug. 16, 2016, 5 pages.
Final Office Action, issued by the United States Patent and Trademark Office in connection with U.S. Appl. No. 12/410,372, dated Aug. 25, 2016, 61 pages.
Notification of Provisional Rejection, issued by the Korean Patent Office in connection with Patent Application No. 10-2010-7001406, dated Jul. 27, 2016, 4 pages (includes partial translation).
Final Office Action, issued by the United States Patent and Trademark Office in connection with U.S. Appl. No. 13/945,357, dated Nov. 1, 2016, 22 pages.
Advisory Action, issued by the United States Patent and Trademark Office in connection with U.S. Appl. No. 12/410,372, dated Nov. 7, 2016, 3 pages.
Examiner's Answer, issued by the United States Patent and Trademark Office in connection with U.S. Appl. No. 12/234,372, dated Nov. 14, 2016, 18 pages.
Examiner's Answer, issued by the United States Patent and Trademark Office in connection with U.S. Appl. No. 12/608,685, dated Nov. 14, 2016, 10 pages.
Final Office Action, issued by the United States Patent and Trademark Office in connection with U.S. Appl. No. 12/884,034, dated Nov. 29, 2016, 27 pages.
First Examination Report, issued by the European Patent Office in connection with European Application No. 08796890.5, dated Sep. 29, 2016, 4 pages.
Final Office Action, issued by the United States Patent and Trademark Office in connection with U.S. Appl. No. 12/410,380, dated Dec. 15, 2016, 31 pages.
Non-Final Office Action, issued by the United States Patent and Trademark Office in connection with U.S. Appl. No. 13/708,344, dated Jan. 26, 2017, 52 pages.
Examiner's Answer, issued by the United States Patent and Trademark Office in connection with U.S. Appl. No. 13/965,805, dated Jan. 31, 2017, 25 pages.
Final Office Action, issued by the United States Patent and Trademark Office in connection with U.S. Appl. No. 12/413,297, dated Feb. 9, 2017, 7 pages.
Advisory Action, issued by the United States Patent and Trademark Office in connection with U.S. Appl. No. 12/884,034, dated Mar. 2, 2017, 14 pages.
English Translation of Notice Prior to Allowance, issued by the Israeli Patent Office in connection with Patent Application No. 201187, dated Feb. 14, 2017, 1 page.
Decision on Appeal, issued by the United States Patent and Trademark Office in connection with U.S. Appl. No. 12/122,253, dated Mar. 31, 2017, 37 pages.
Non-Final Office Action, issued by the United States Patent and Trademark Office in connection with U.S. Appl. No. 13/708,525, dated Apr. 27, 2017, 45 pages.
Examiner's Answer, issued by the United States Patent and Trademark Office in connection with U.S. Appl. No. 12/410,372, dated May 25, 2017, 9 pages.
Decision on Appeal, issued by the United States Patent and Trademark Office in connection with U.S. Appl. No. 12/546,586, dated Jun. 5, 2017, 39 pages.
European Patent Office, "Communication Pursuant to Article 94(3) EPC," issued in connection with European Patent Application No. 08 744 383.4, dated Apr. 19, 2017, 6 pages.
Final Office Action, issued by the United States Patent and Trademark Office in connection with U.S. Appl. No. 13/708,344, dated Jun. 29, 2017, 38 pages.
Non-Final Office Action, issued by the United States Patent and Trademark Office in connection with U.S. Appl. No. 13/945,357, dated Jul. 6, 2017, 17 pages.
Decision on Appeal, issued by the United States Patent and Trademark Office in connection with U.S. Appl. No. 12/113,870, dated Jul. 13, 2017, 12 pages.

(56) References Cited

OTHER PUBLICATIONS

Final Office Action, issued by the United States Patent and Trademark Office in connection with U.S. Appl. No. 13/708,525, dated Aug. 14, 2017, 38 pages.
Examiner's Answer, issued by the United States Patent and Trademark Office in connection with U.S. Appl. No. 12/410,380, dated Aug. 18, 2017, 2017, 11 pages.
Non-Final Office Action, issued by the United States Patent and Trademark Office in connection with U.S. Appl. No. 12/546,586, dated Sep. 19, 2017, 43 pages.
Notice of Allowance, issued by the United States Patent and Trademark Office in connection with U.S. Appl. No. 12/113,870, dated Sep. 26, 2017, 51 pages.
Summons to Attend Oral Proceedings Pursuant to Rule 115(1) EPC, issued by the European Patent Office in connection with European Patent Application No. 08796890.5, dated Jul. 3, 2017, 3 pages.
English Translation of First Examination Report, issued by the Indian Patent Office in connection with Indian Patent Application No. 6145/CHENP/2009, dated Aug. 16, 2017, 6 pages.
Advisory Action, issued by the United States Patent and Trademark Office in connection with U.S. Appl. No. 13/708,344, dated Oct. 2, 2017, 5 pages.
Final Office Action, issued by the United States Patent and Trademark Office in connection with U.S. Appl. No. 13/945,357, dated Oct. 20, 2017, 16 pages.
Advisory Action, issued by the United States Patent and Trademark Office in connection with U.S. Appl. No. 13/708,525, dated Oct. 26, 2017, 4 pages.
Examiner's Answer, issued by the United States Patent and Trademark Office in connection with U.S. Appl. No. 12/413,297, dated Oct. 31, 2017, 2017, 68 pages.
Non-Final Office Action, issued by the United States Patent and Trademark Office in connection with U.S. Appl. No. 15/299,752, dated Nov. 3, 2017, 131 pages.
Non-Final Office Action, issued by the United States Patent and Trademark Office in connection with U.S. Appl. No. 12/884,034, dated Nov. 15, 2017, 49 pages.
Decision on Appeal, issued by the United States Patent and Trademark Office in connection with U.S. Appl. No. 13/730,541, dated Dec. 6, 2017, 14 pages.
Non-Final Office Action, issued by the United States Patent and Trademark Office in connection with U.S. Appl. No. 12/546,586, dated Dec. 28, 2017, 23 pages.
Decision on Appeal, issued by the United States Patent and Trademark Office in connection with U.S. Appl. No. 12/608,685, dated Jan. 29, 2018, 11 pages.
Ganel et al., "The Relationship Between fMRI Adapation and Repetition Priming," NeuroImage, Jul. 18, 2006, pp. 1434-1440, 9 pages.
Non-Final Office Action, issued by the United States Patent and Trademark Office in connection with U.S. Appl. No. 13/730,511, dated Jan. 30, 2014, 67 pages.
Non-Final Office Action, issued by the United States Patent and Trademark Office in connection with U.S. Appl. No. 13/730,511, dated Aug. 13, 2014, 8 pages.
Final Office Action, issued by the United States Patent and Trademark Office in connection with U.S. Appl. No. 13/730,511, dated May 6, 2015, 15 pages.
Examiner's Answer, issued by the United States Patent and Trademark Office in connection with U.S. Appl. No. 13/730,511, dated Feb. 18, 2016, 5 pages.
Decision on Appeal, issued by the United States Patent and Trademark Office in connection with U.S. Appl. No. 13/730,511, dated Mar. 1, 2018, 14 pages.
Notice of Allowance, issued by the United States Patent and Trademark Office in connection with U.S. Appl. No. 13/730,511, dated May 29, 2014, 8 pages.
Final Office Action, issued by the United States Patent and Trademark Office in connection with U.S. Appl. No. 13/730,541, dated Feb. 12, 2015, 6 pages.
Decision on Appeal, issued by the United States Patent and Trademark Office in connection with U.S. Appl. No. 12/410,380, dated Mar. 30, 2015, 6 pages.
Decision on Appeal, issued by the United States Patent and Trademark Office in connection with U.S. Appl. No. 12/234,372, dated Jun. 15, 2015, 5 pages.
Non-Final Office Action, issued by the United States Patent and Trademark Office in connection with U.S. Appl. No. 12/234,372, dated Sep. 23, 2015, 16 pages.
Decision on Appeal, issued by the United States Patent and Trademark Office in connection with U.S. Appl. No. 12/410,372, dated Sep. 22, 2015, 6 pages.
Decision on Appeal, issued by the United States Patent and Trademark Office in connection with U.S. Appl. No. 12/413,297 , dated Nov. 27, 2015, 5 pages.
Decision on Appeal, issued by the United States Patent and Trademark Office in connection with U.S. Appl. No. 13/730,564, dated Feb. 2, 2018, 10 pages.
Decision on Appeal, issued by the United States Patent and Trademark Office in connection with U.S. Appl. No. 13/730,550, dated Mar. 27, 2018, 13 pages.
Notice of Allowance, issued by the United States Patent and Trademark Office in connection with U.S. Appl. No. 15/299,752, dated Apr. 17, 2017, 21 pages.
Non-Final Office Action, issued by the United States Patent and Tmdemark Office in connection with U.S. Appl. No. 12/884,034, dated May 3, 2018, 46 pages.
Non-Final Office Action, issued by the United States Patent and Tmdemark Office in connection with U.S. Appl. No. 13/708,525, dated May 18, 2018, 31 pages.
Notice of Allowance, issued by the United States Patent and Trademark Office in connection with U.S. Appl. No. 13/730,541, dated Jun. 27, 2017, 62 pages.
Notice of Allowance, issued by the United States Patent and Trademark Office in connection with U.S. Appl. No. 13/730,564, dated Jun. 27, 2017, 69 pages.
Final Office Action, issued by the United States Patent and Trademark Office in connection with U.S. Appl. No. 12/546,586, dated Jun. 28, 2018, 22 pages.
Decision on Request for Rehearing, issued by the United States Patent and Trademark Office in connection with U.S. Appl. No. 12/608,685, dated Aug. 10, 2018, 8 pages.
Extended European Search Report, issued by the European Patent Office in connection with European Application No. 08747389.8-1952, dated Sep. 25, 2015, 6 pages.
English Translation of First Examination Report, issued by the Indian Patent Office in connection with Indian Patent Application No. 4438/KOLNP/2009, dated Sep. 25, 2017, 7 pages.
Communication Under Rule 71(3) EPC, issued by the European Patent Office in connection with European Application No. 08796890. 5, dated Mar. 16, 2018, 43 pages.
English Translation of First Examination Report, issued by the Indian Patent Office in connection with Indian Patent Application No. 4441/KOLNP/2009, dated May 21, 2018, 5 pages.
Knutson et al., "Neural Predictors of Purchases," Neuron vol. 53 (Jan. 4, 2007), pp. 147-156, 10 pages.
Schaefer et al., "Neural Correlates of Culturally Familiar Brands of Car Manufacturers," NeuroImage, vol. 31 (2006), pp. 861-865, 5 pages.
Aharon et al., "Beautiful Faces Have Variable Reward Value: fMRI and Behavorial Evidence," Neuron, vol. 32 (2001), pp. 537-551, 15 pages.
Hall, Bruce F., "A New Model for Measuring Advertising Effectiveness," Journal of Advertising Research, Mar.-Apr. 2002, 10 pages.
Kamba et al., "The Krakatoa Chronicle—An Interactive, Personalized, Newspaper on the Web," available at: http://www.w3.org/Conferences/WWW4/Papers/93/ (last accessed Nov. 2, 2015), 15 pages.
Ehrenberg et al., "Understanding Brand Performance Measures: Using Dirichlet Benchmarks," 2004, Journal of Business Research, vol. 57, pp. 1307-1325, 19 pages.

(56) References Cited

OTHER PUBLICATIONS

Leeflang et al., "Building Models for Marketing Decisions," 2000, Springer Science + Business Media, pp. 192-235, 482-521, 86 pages.
Bhattacharya, "Is your brands loyalty too much, too little, or just right?: Explaining deviations in loyalty from the Dirichlet norm," 1997, International Journal of Research in Marketing, vol. 14, pp. 421-435, 15 pages.
McCraty et al., "Impact of a Workplace Stress Reduction Program on Blood Pressure and Emotional Health in Hypertensive Employees", the Journal of Alternative and Complementary Medicine, vol. 9, No. 3, 2003, pp. 355-369, Mary Ann Liebert, Inc., 15 pages.
Nikolaeva et al., "The Moderating Role of Consumer and Product Characteristics on the Value of Customized On-Line Recommendations," 2006, International Journal of Electronic Commerce, vol. 11, No. 2, pp. 101-123, 24 pages.
Ehrenberg, "New Brands and the Existing Market," 1991, International Journal of Market Research, vol. 33, No. 4, 10 pages.
Foxall, "The Substitutability of Brands," 1999, Managerial and Decision Economics, vol. 20, pp. 241-257, 17 pages.
Pammer et al., "Forecasting the Penetration of a New Product—A Bayesian Approach," 2000, Journal of Business and Economic Statistics, vol. 18, No. 4, pp. 428-435, 8 pages.
Rungie et al., "Calculation of Theoretical Brand Performance Measures from the Parameters of the Dirichlet Model," 2004, Marketing Bulletin, Massey University, 15, Technical Note 2, pp. 1-19, 20 pages.
Uncles et al., "Patterns of Buyer Behavior: Regularities, Models, and Extensions," 1995, Marketing Science, vol. 14, No. 3, pp. G71-G78, 9 pages.
Boltz, "The cognitive processing of film and musical soundtracks," Haverford College, Haverford, Pennsylvania, 2004, 32 (7), 1194-1205, 12 pages.
Christie et al., "Autonomic specificity of discrete emotion and dimensions of affective space: a multivariate approach," International Journal of Psychophysiology, 51 (2004) 143-153, 11 pages.
Coombes et al., "Emotion and movement: Activation of defensive circuitry alters the magnitude of a sustained muscle contraction," University of Florida, USA, Neuroscience Letters 396 (2006) 192-196, 5 pages.
Cryer et al. "Pull the Plug on Stress," Harvard Business Review, Jul. 2003, 8 pages.
Demaree et al., "Predicting facial valence to negative stimuli from resting RSA: Not a function of active emotion regulation," Cognition and Emotion vol. 20, Issue 2, 2006, pp. 161-176, published on Sep. 9, 2010, http://www.tandfonline.com/doi/abs/10.1080/02699930500260427, 6 pages. (Abstract provided.).
Elkman et al., "Autonomic Nervous System Activity Distinguishes among Emotions," Science, New Series, vol. 221, No. 4616. (Sep. 16, 1983), pp. 1208-1210, http://links.jstor.org/sici?sici=0036-8075%2819830916%293%3A221%3A4616%3C1208%3AANSADA%3E2.0.CO%3B2-H, 5 pages.
Elton, "Measuring emotion at the symphony," The Boston Globe, Apr. 5, 2006, http://www.psych.mcgill.ca/labs/levitin/media/measuring_emotion_boston.html, 3 pages.
Goldberg, "Getting wired could help predict emotions," The Boston Globe, Jun. 13, 2005, http://www.boston.com/yourlife/health/mental/articles/2005/06/13/getting_wired_could_help_predict_emotions/?page=full, 4 pages.
Gomez et al., "Respiratory Responses Associated with Affective Processing of Film Stimuli," Biological Psychology, vol. 68, Issue 3, Mar. 2005, pp. 223-235, 2 pages (Abstract provided.).
Hall, "Is cognitive processing the right dimension," World Advertising Research Center, Jan. 2003, 3 pages.
Hall, "On Measuring the Power of Communications," Journal of Advertising Research, 44, pp. 1-11, doi:10.1017/S0021849904040139, (2004), 1 page (Abstract provided.).
Hall, "Research and strategy: a fall from grace," ADMAP, Issue 443, pp. 18-20, 2003, 1 page. (Abstract provided).
Hubert et al., "Autonomic, neuroendocrine, and subjective responses to emotion-inducing film stimuli," Int J Psychophysiol,Aug. 1991, 2 pages. (Abstract provided.).
Levenson et al., "Emotion and Autonomic Nervous System Activity in the Minangkabau of West Sumatra," Department of Psychology, University of California, Berkeley, Journal of Personality and Social Psychology, 1992, 2 pages. (Abstract provided.).
Marci et al., "The effect of emotional distance on psychophysiologic concordance and perceived empathy between patient and interviewer," Applied Psychophysiology and Biofeedback, Jun. 2006, vol. 31, issue 2, 31:115-129, 8 pages. (Abstract provided.).
McCraty et al., "Analysis of twenty-four hour heart rate variability in patients with panic disorder," Biological Psychology, vol. 56, Issue 2, Jun. 2001, pp. 131-150, 1 page. (Abstract provided.).
McCraty et al., "Electrophysiological Evidence of Intuition: Part 1. The Surprising Role of the Heart," The Journal of Alternative and Complementary Medicine, vol. 10, No. 1, 2004, pp. 133-143, Mary Ann Liebert, Inc., 12 pages.
McCraty et al., "Electrophysiological Evidence of Intuition: Part 2. A System-Wide Process?," The Journal of Alternative and Complementary Medicine, vol. 10, No. 2, 2004, pp. 325-336, Mary Ann Liebert, Inc., 12 pages.
McCraty et al., "The Effects of Different Types of Music on Mood, Tension, and Mental Clarity," Original Research, Alternative Therapies, Jan. 1998, vol. 4., No. 1, pp. 75-84, 10 pages.
McCraty et al., "The Effects of Emotions on Short-Tem Power Spectrum Analysis of Heart Rate Variability," American Journal of Cardiology, vol. 76, No. 14, Nov. 15, 1995, pp. 1089-1093, 6 pages.
McCraty et al., "The Impact of a New Emotional Self-Management Program on Stress, Emotions, Heart Rate Variability, DHEA and Cortisol," Integrative Physiological and Behavioral Science, Apr.-Jun. 1998, vol. 33, No. 2, 151-170, 20 pages.
McCraty et al., "The Impact of an Emotional Self-Management Skills Course on Psychosocial Functioning and Autonomic Recovery to Stress in Middle School Children," Integrative Physiological and Behavioral Science, Oct.-Dec. 1999, vol. 34, No. 4, 246-268, 23 pages.
Melillo, "Inside the Consumer Mind; What Neuroscience Can Tell Us About Marketing," Adweek, Public Citizen's Commercial Alert, Jan. 16, 2006, http://www.adweek.com/news/advertising/inside-consumer-mind-83549, 8 pages.
Miller et al., "Influence of Specific Emotional States on Autonomic Reactivity and Pulmonary Function in Asthmatic Children," Journal of the American Academy of Child & Adolescent Psychiatry, vol. 36, Issue 5, May 1997, pp. 669-677, 3 pages. (Abstract provided).
Murphy et al., "The Heart Reinnervates After Transplantation," Official Journal of the Society of Thoracic Surgeons and the Southern Thoracic Surgical Association, Jun. 2000, vol. 69, Issue 6, pp. 1769-1781, 13 pages.
Rosenberg, "Emotional R.O.I.," The Hub, May/Jun. 2006,pp. 24-25, 2 pages.
Tiller et al., "Cardiac Coherence: A New, Noninvasive Measure of Autonomic Nervous System Order," Alternative Therapies, Jan. 1996, vol. 2, No. 1, 14 pages.
Umetani et al. "Twenty-Four Hour Time Domain Heart Rate Variability and Heart Rate: Relations to Age and Gender Over Nine Decades," J Am Coll Cardiol, Mar. 1, 1998, pp. 593-601, 9 pages.
Von Leupoldt et al., "Emotions in a Body Plethysmograph," Journal of Psychophysiology (2004), 18, pp. 170-176, 1 page. (Abstract provided.).
Kallman, "Effect of Blank Time on Picture Recognition," The American Journal of Psychology, vol. 97, No. 3 (Autumn, 1984), pp. 399-406, 4 pages. (Abstract provided.).
Larose, *Data Mining Methods and Models*, Department of Mathematical Sciences, Central Connecticut State University, www.dbeBooks.com—An Ebook Library,published by John Wiley & Sons, Inc., 2006, 340 pages. (Book, copy not provided.).
Han et al., *Data Mining: Concepts and Techniques*, $2^{nd}$ Edition, Elsevier, 2006, 772 pages. (Book, copy not provided.).
Liu et al., *Web Data Mining: Exploring Hyperlinks, Contents, and Usage Data*, Springer Science & Business Media, 2007, 532 pages, (Book, copy not provided.).

(56) References Cited

OTHER PUBLICATIONS

Berry et al., *Data Mining Techniques: For Marketing Sales and Customer Support*, Wiley Publishing Inc., Jun. 1997, 464 pages. (Book, copy not provided.).
Horovitz, "Watching Ads Is Real Science Research Companies Monitor Physiological Reactions to Commercials to Determine Their Effectiveness," Los Angeles Times, Sep. 1, 1991, 3 pages.
Sung et al., "Wearable feedback systems for rehabilitation," Journal of NeuroEngineering and Rehabilitation, Jun. 29, 2005, 12 pages.
Jaffe, *Casting for Big Ideas*, Adweek Magazine Series, Book 8, 2003, 256 page. (Book, copy not provided).
Hall, "Advertising as a Factor of Production," ADMAP, 2003, pp. 47-49, 1 page. (Abstract provided.).
Ranii, "Adding Science to Gut Check," The News & Observer, D3 (Apr. 6, 2005), 1 page. (Abstract provided.).
Advisory action, issued by the United States Patent and Trademark Office in connection with U.S. Appl. No. 12/608,660, dated Oct. 26, 2012, 3 pages.
Decision on Appeal, issued by the United States Patent and Trademark Office in connection with U.S. Appl. No. 13/965,805, dated Sep. 10, 2018, 10 pages.
Decision on Appeal, issued by the United States Patent and Trademark Office in connection with U.S. Appl. No. 12/234,372, dated Sep. 19, 2018, 8 pages.
Advisory Action, issued by the United States Patent and Trademark Office in connection with U.S. Appl. No. 12/546,586, dated Oct. 1, 2018, 17 pages.
Non-Final Office Action, issued by the United States Patent and Trademark Office in connection with U.S. Appl. No. 16/037,666, dated Oct. 4, 2018, 37 pages.
Final Office Action, issued by the United States Patent and Trademark Office in connection with U.S. Appl. No. 13/708,525, dated Oct. 5, 2018, 31 pages.
Notice of Allowance, issued by the United States Patent and Trademark Office in connection with U.S. Appl. No. 16/037,666, dated Dec. 6, 2018, 96 pages.
Decision on Appeal, issued by the United States Patent and Trademark Office in connection with U.S. Appl. No. 12/410,372, dated Dec. 28, 2018, 8 pages.
Decision on Request for Rehearing, issued by the United States Patent and Trademark Office in connection with U.S. Appl. No. 12/410,372, dated Mar. 27, 2019, 7 pages.
Decision on Appeal, issued by the United States Patent and Trademark Office in connection with U.S. Appl. No. 12/410,380, dated Jul. 8, 2019, 12 pages.
Decision on Appeal, issued by the United States Patent and Trademark Office in connection with U.S. Appl. No. 12/413,297, dated Sep. 24, 2019, 15 pages.
Summons to Attend Oral Proceedings Pursuant to Rule 115(1) EPC, issued by the European Patent Office in connection with European Patent Application No. 08744383.4, dated Dec. 11, 2018, 6 pages.
Intimation of Grant and Recordal of Patent, issued by the Indian Patent Office in connection with Indian Patent Application No. 4438/KOLNP/2009, dated Jul. 3, 2019, 1 page.
Intimation of Grant and Recordal of Patent, issued by the Indian Patent Office in connection with Indian Patent Application No. 4441/KOLNP/2009, dated Sep. 3, 2019, 1 page.
Non-Final Office Action, issued by the United States Patent and Trademark Office in connection with U.S. Appl. No. 15/967,939, dated Oct. 4, 2019, 5 pages.
Notice of Allowance, issued by the United States Patent and Trademark Office in connection with U.S. Appl. No. 15/989,987, dated Oct. 17, 2019, 8 pages.
Non-Final Office Action, issued by the United States Patent and Trademark Office in connection with U.S. Appl. No. 16/183,131, dated Nov. 18, 2019, 5 pages.
Non-Final Office Action, issued by the United States Patent and Trademark Office in connection with U.S. Appl. No. 12/546,586, dated Jan. 22, 2020, 12 pages.
Notice of Allowance, issued by the United States Patent and Trademark Office in connection with U.S. Appl. No. 15/967,939, dated Jan. 29, 2020, 8 pages.
Notice of Allowance, issued by the United States Patent and Trademark Office in connection with U.S. Appl. No. 16/183,131, dated Mar. 24, 2020, 8 pages.
Non-Final Office Action, issued by the United States Patent and Trademark Office in connection with U.S. Appl. No. 16/151,044, dated Apr. 2, 2020, 5 pages.
Non-Final Office Action, issued by the United States Patent and Trademark Office in connection with U.S. Appl. No. 16/151,050, dated Apr. 6, 2020, 13 pages.
Final Office Action, issued by the United States Patent and Trademark Office in connection with U.S. Appl. No. 12/546,586, dated Jul. 24, 2020, 14 pages.
Non-Final Office Action, issued by the United States Patent and Trademark Office in connection with U.S. Appl. No. 16/193,930, dated Jul. 27, 2020, 12 pages.
Non-Final Office Action, issued by the United States Patent and Trademark Office in connection with U.S. Appl. No. 16/421,864, dated Aug. 13, 2020, 24 pages.
Final Office Action, issued by the United States Patent and Trademark Office in connection with U.S. Appl. No. 16/151,050, dated Oct. 7, 2020, 5 pages.
Notice of Allowance, issued by the United States Patent and Trademark Office in connection with U.S. Appl. No. 16/151,044, dated Oct. 9, 2020, 8 pages.
Notice of Allowance, issued by the United States Patent and Trademark Office in connection with U.S. Appl. No. 16/193,930, dated Nov. 18, 2020, 8 pages.
Notice of Allowance, issued by the United States Patent and Trademark Office in connection with U.S. Appl. No. 12/546,586, dated Dec. 9, 2020, 8 pages.
Notice of Allowance, issued by the United States Patent and Trademark Office in connection with U.S. Appl. No. 16/151,050, dated Jan. 22, 2021, 8 pages.
Final Office Action, issued by the United States Patent and Trademark Office in connection with U.S. Appl. No. 16/421,864, dated Jan. 25, 2021, 26 pages.
Hearing Notice issued by the Indian Patent Office in connection with Indian Patent Application No. 6145/CHENP/2009, dated Mar. 12, 2020, 2 pages.
Kim et al., "Design for an Interactive Television Advertising System," Proceedings for the 39th Hawaii International Conference on System Sciences (2006), 9 pages.
"One to One Interactive and Innerscope Research Release Preliminary Biomeasures Study Results," PR Newswire, Feb. 28, 2007, 4 pages.
Non-Final Office Action, issued by the United States Patent and Trademark Office in connection with U.S. Appl. No. 16/692,511, dated Feb. 24, 2021, 12 pages.
Non-Final Office Action, issued by the United States Patent and Trademark Office in connection with U.S. Appl. No. 16/360,282, dated Mar. 18, 2021, 7 pages.
Non-Final Office Action, issued by the United States Patent and Trademark Office in connection with U.S. Appl. No. 16/421,864, dated Apr. 22, 2021, 18 pages.

* cited by examiner

| Dataset Data Model 301 | | | | | |
|---|---|---|---|---|---|
| Experiment Name 303 | Client Attributes 305 | Subject Pool 307 | Logistics Information 309 | Stimulus Material 311 | ... |

| Subject Attributes Data Model 315 | | | |
|---|---|---|---|
| Subject Name 317 | Demographic Attributes 319 | Contact Information 321 | ... |

| Neuro-Feedback Association Data Model 325 | | | |
|---|---|---|---|
| Experiment Protocols 327 | Modalities included 329 | Experiment Design Parameters 333 | ... |

| Data Collection Data Model 337 | | | | |
|---|---|---|---|---|
| Recording Attributes 339 | Equipment Attributes 341 | Modalities Recorded 343 | Data Storage Attributes 345 | ... |

| Preset Query Data Model 349 | | | | |
|---|---|---|---|---|
| Query Name 351 | Accessed Data Collection 353 | Access Security Attributes 355 | Refresh Attributes 357 | ... |

Figure 3

| Subject Attributes Queries 415 | |
|---|---|
| Location 417 | Demographic Attributes 419 | Session Information 421 | ... |

Subject Attributes Queries 415

| Location 417 | Demographic Attributes 419 | Session Information 421 | ... |
|---|---|---|---|

Experimental Design Queries 425

| Experiment Protocols 427 | Product Category 429 | Surveys Included 431 | Stimulus Used 433 | ... |
|---|---|---|---|---|

Response Assessment Queries 437

| Attention Score 439 | Emotion Score 441 | Retention Score 443 | Effectiveness Score 445 | ... |
|---|---|---|---|---|

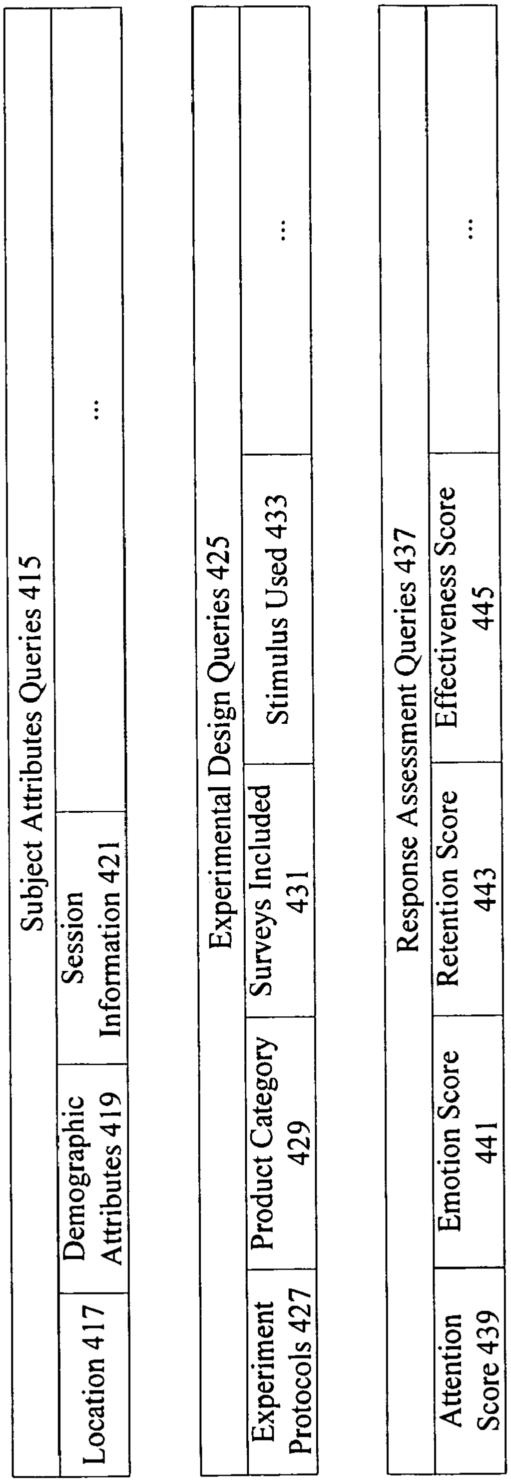

Figure 4

Client Assessment Summary Reports 501

| Effectiveness 503 | Component Assessment 505 | Audience Response 507 | ... |
|---|---|---|---|

Client Cumulative Reports 511

| Media Grouped 513 | Campaign Grouped 515 | Time/Location Grouped 517 | ... |
|---|---|---|---|

Industry Cumulative And Syndicated Reports 521

| Aggregate Assessment 523 | Top Performers 525 | Bottom Performers 527 | Outliers 529 | Trend 531 | ... |
|---|---|---|---|---|---|

NEURO-PHYSIOLOGY AND NEURO-BEHAVIORAL BASED STIMULUS TARGETING SYSTEM

CROSS-REFERENCE TO RELATED APPLICATIONS

This patent arises from a continuation of U.S. patent application Ser. No. 15/989,987, filed on May 25, 2018, and issued as U.S. Pat. No. 10,580,031, which arises from a continuation of U.S. patent application Ser. No. 13/730,550, filed on Dec. 28, 2012 (now abandoned), which arises from a continuation of U.S. patent application Ser. No. 12/122,262, filed on May 16, 2008, and issued as U.S. Pat. No. 8,392,253, and claims the benefit under 35 U.S.C. § 119(e) to U.S. Provisional Patent Application Ser. No. 60/938,286, which was filed on May 16, 2007. U.S. patent application Ser. No. 15/989,987, U.S. patent application Ser. No. 13/730,550, U.S. patent application Ser. No. 12/122,262, and U.S. Provisional Patent Application Ser. No. 60/938,286 are all hereby incorporated herein by reference in their entireties.

FIELD OF THE DISCLOSURE

The present disclosure relates to a neuro-physiology and neuro-behavior based stimulus target system.

BACKGROUND

Conventional systems for selectively targeting stimulus materials such as advertising often rely on general geographic, demographic, or statistical information. In some instances, conventional system selectively target stimulus materials using survey based response collection. However, these mechanisms for selectively targeting stimulus materials are limited.

BRIEF DESCRIPTION OF THE DRAWINGS

The disclosure may best be understood by reference to the following description taken in conjunction with the accompanying drawings, which illustrate particular examples.

FIG. 3 illustrates examples of data models that can be used with the stimulus targeting system.

FIG. 4 illustrates one example of a query that can be used with the stimulus targeting system.

DETAILED DESCRIPTION

Figure 1:
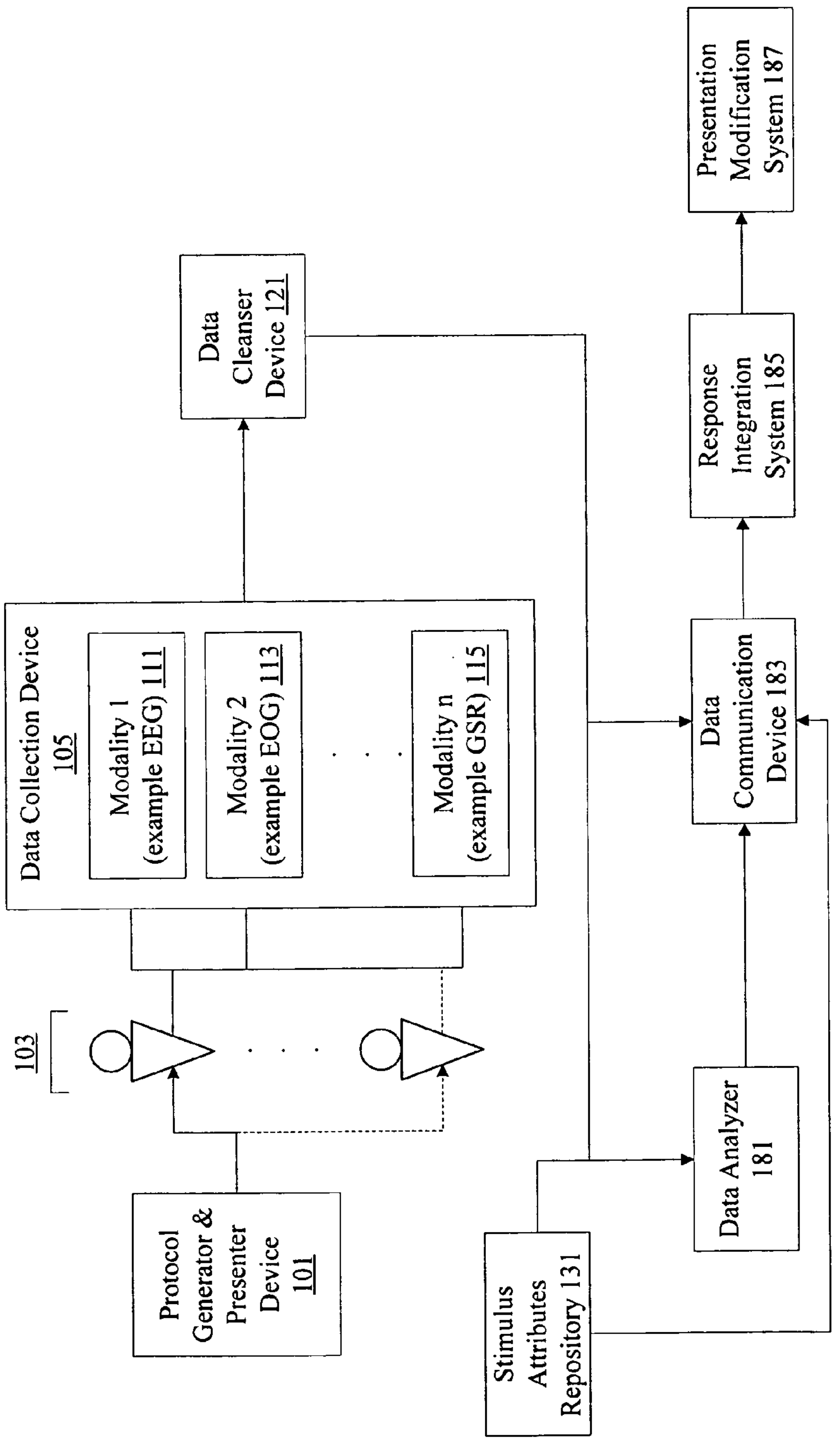
FIG. 1 illustrates one example of a system for performing stimulus targeting.

Reference will now be made in detail to some specific examples of the disclosure including the best modes contemplated by the inventors for carrying out the teachings of the disclosure. Examples of these specific examples are illustrated in the accompanying drawings. While the disclosure is described in conjunction with these specific examples, it will be understood that it is not intended to limit the disclosure to the described examples. On the contrary, it is intended to cover alternatives, modifications, and equivalents as may be included within the spirit and scope of the disclosure as defined by the appended claims.

For example, the techniques and mechanisms of the present disclosure will be described in the context of particular types of neuro-physiological and neuro-behavioral data. However, it should be noted that the techniques and mechanisms of the present disclosure apply to a variety of different types of data. It should be noted that various mechanisms and techniques can be applied to any type of stimuli. In the following description, numerous specific details are set forth in order to provide a thorough understanding of the present disclosure. Particular examples of the present disclosure may be implemented without some or all of these specific details. In other instances, well known process operations have not been described in detail in order not to unnecessarily obscure the present disclosure.

Various techniques and mechanisms of the present disclosure will sometimes be described in singular form for clarity. However, it should be noted that some examples include multiple iterations of a technique or multiple instantiations of a mechanism unless noted otherwise. For example, a system uses a processor in a variety of contexts. However, it will be appreciated that a system can use multiple processors while remaining within the scope of the present disclosure unless otherwise noted. Furthermore, the techniques and mechanisms of the present disclosure will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

OVERVIEW

Consequently, it is desirable to provide improved methods and apparatus for providing a stimulus targeting system.

A system performs stimulus targeting using neuro-physiological and neuro-behavioral data. Subjects are exposed to stimulus material such as marketing and entertainment materials and data is collected using mechanisms such as Electroencephalography (EEG), Galvanic Skin Response (GSR), Electrocardiograms (EKG), Electrooculography (EOG), eye tracking, and facial emotion encoding. Neuro-physiological and neuro-behavioral data collected is analyzed to select targeted stimulus materials. The targeted stimulus materials are provided to particular subjects for a variety of purposes.

EXAMPLES

Conventional stimulus targeting systems typically target general geographic areas and demographic groups and do not have the resolution to target narrow audiences or individuals. Some efforts have been made to selectively target narrow audiences or individuals, but these efforts have been limited because of a variety of reasons.

For example, subjects are required to complete surveys after initial and subsequent exposures to stimulus material such as an advertisement. The survey responses are analyzed to determine possible patterns. However, survey results often provide only limited information. For example, survey subjects may be unable or unwilling to express their true thoughts and feelings about a topic, or questions may be phrased with built in bias. Articulate subjects may be given more weight than non-expressive ones. Analysis of multiple survey responses and correlation of the responses to stimulus material is also limited. A variety of semantic, syntactic, metaphorical, cultural, social and interpretive biases and errors prevent accurate and repeatable evaluation.

Consequently, the techniques and mechanisms of the present disclosure use neuro-physiological and neuro-behavioral response measurements such as central nervous system, autonomic nervous system, and effector measurements to improve stimulus targeting. Some examples of central nervous system measurement mechanisms include Functional Magnetic Resonance Imaging (fMRI) and Electroencephalography (EEG). fMRI measures blood oxygenation in the brain that correlates with increased neural activity. However, current implementations of fMRI have poor temporal resolution of few seconds. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly.

Autonomic nervous system measurement mechanisms include Galvanic Skin Response (GSR), Electrocardiograms (EKG), pupillary dilation, etc. Effector measurement mechanisms include Electrooculography (EOG), eye tracking, facial emotion encoding, reaction time etc.

According to various examples, the techniques and mechanisms of the present disclosure intelligently blend multiple modes and manifestations of precognitive neural signatures with cognitive neural signatures and post cognitive neurophysiological manifestations to more accurately allow selective targeting of stimulus materials. In some examples, autonomic nervous system measures are themselves used to validate central nervous system measures. Effector and behavior responses are blended and combined with other measures. According to various examples, central nervous system, autonomic nervous system, and effector system measurements are aggregated into a measurement that allows selective targeting of stimulus materials.

In particular examples, multiple subjects are exposed to stimulus material and data such as neuro-physiological and neuro-behavioral data. According to various examples, the multiple subjects may be exposed simultaneously to stimulus material in a large group setting, in multiple small group settings, in relatively isolated settings, etc. The multiple subjects may or may not be allowed to interact directly or indirectly. Response data collected during exposure of the multiple subjects is analyzed and integrated to determine neuro-physiological and neuro-behavioral response data. According to various examples, response data is analyzed and enhanced for each subject and further analyzed and enhanced by integrating data across multiple subjects to select stimulus materials to provide to particular subjects.

According to various examples, neuro-physiological and neuro-behavioral data may show particular effectiveness of stimulus material for a particular subset of individuals. In particular examples, neuro-physiological and neuro-behavioral data may show profiles of responses for particular subjects based on attributes of the stimulus material. Targeted stimulus materials may be intelligently selected using neuro-physiological and neuro-behavioral data and known attributes of the stimulus materials. In some examples, survey results and focus group information can also be used to elicit further insights on selecting stimulus materials. The additional stimulus materials selected may be used to obtain additional neuro-physiological and neuro-behavioral information from particular subjects. The additional stimulus materials may also be selected as materials that would be particularly effective in an advertising campaign or mailing campaign. Stimulus materials may be targeted to narrow audiences, individuals, or even specific subgroups or larger populations.

A variety of stimulus materials such as entertainment and marketing materials, media streams, billboards, print advertisements, text streams, music, performances, sensory experiences, etc. can be analyzed. According to various examples, enhanced neuro-physiological and neuro-behavioral data is generated using a data analyzer that performs both intra-modality measurement enhancements and cross-modality measurement enhancements. According to various examples, brain activity is measured not just to determine the regions of activity, but to determine interactions and types of interactions between various regions. The techniques and mechanisms of the present disclosure recognize that interactions between neural regions support orchestrated and organized behavior. Attention, emotion, memory, and other abilities are not merely based on one part of the brain but instead rely on network interactions between brain regions.

The techniques and mechanisms of the present disclosure further recognize that different frequency bands used for multi-regional communication can be indicative of the effectiveness of stimuli. In particular examples, evaluations are calibrated to each subject and synchronized across subjects. In particular examples, templates are created for subjects to create a baseline for measuring pre and post stimulus differentials. According to various examples, stimulus generators are intelligent and adaptively modify specific parameters such as exposure length and duration for each subject being analyzed. An intelligent stimulus generation mechanism intelligently adapts output for particular users and purposes. A variety of modalities can be used including EEG, GSR, EKG, pupillary dilation, EOG, eye tracking, facial emotion encoding, reaction time, etc. Individual modalities such as EEG are enhanced by intelligently recognizing neural region communication pathways.

Cross modality analysis is enhanced using a synthesis and analytical blending of central nervous system, autonomic nervous system, and effector signatures. Synthesis and analysis by mechanisms such as time and phase shifting, correlating, and validating intra-modal determinations allow generation of a composite output characterizing the significance of various data responses. Responses can be integrated across subjects and additional stimulus material can be targeted to particular subjects and groups using responses and stimulus material attributes.

FIG. 1 illustrates one example of a system for performing stimulus targeting using central nervous system, autonomic nervous system, and effector measures. According to various examples, the stimulus targeting system includes a protocol generator and presenter device 101. In particular examples, the protocol generator and presenter device 101 is merely a presenter device and merely presents stimulus material to a user. The stimulus material may be a media clip, a commercial, pages of text, a brand image, a performance, a magazine advertisement, a movie, an audio presentation, particular tastes, smells, textures and/or sounds. The stimuli can involve a variety of senses and occur with or without human supervision. Continuous and discrete modes are supported. According to various examples, the protocol generator and presenter device 101 also has protocol generation capability to allow intelligent customization of stimuli provided to multiple subjects.

According to various examples, the subjects are connected to data collection devices 105. The data collection devices 105 may include a variety of neuro-physiological and neuro-behavioral measurement mechanisms such as EEG, EOG, GSR, EKG, pupillary dilation, eye tracking, facial emotion encoding, and reaction time devices, etc. According to various examples, neuro-physiological and neuro-behavioral data includes central nervous system, autonomic nervous system, and effector data. In particular examples, the data collection devices 105 include EEG 111, EOG 113, and GSR 115. In some instances, only a single data collection device is used. Data collection may proceed with or without human supervision.

The data collection device 105 collects neuro-physiological and neuro-behavioral data from multiple sources. This includes a combination of devices such as central nervous system sources (EEG), autonomic nervous system sources (GSR, EKG, pupillary dilation), and effector sources (EOG, eye tracking, facial emotion encoding, reaction time). In particular examples, data collected is digitally sampled and stored for later analysis. In particular examples, the data collected could be analyzed in real-time. According to particular examples, the digital sampling rates are adaptively chosen based on the neurophysiological and neurological data being measured.

In one particular example, the stimulus targeting system includes EEG 111 measurements made using scalp level electrodes, EOG 113 measurements made using shielded electrodes to track eye data, GSR 115 measurements performed using a differential measurement system, a facial muscular measurement through shielded electrodes placed at specific locations on the face, and a facial affect graphic and video analyzer adaptively derived for each individual.

In particular examples, the data collection devices are clock synchronized with a protocol generator and presenter device 101. The data collection system 105 can collect data from individual subjects (1 system), or can be modified to collect synchronized data from multiple subjects (N+1 system). The N+1 system may include multiple individuals synchronously tested in isolation or in a group setting. In particular examples, the subjects are placed in a large group setting and are allowed to interact while being exposed to the stimulus material. In other examples, subjects are placed in a group setting but are allowed only non-verbal interaction. In still other examples, subjects are not allowed to interact during exposure to stimulus materials. A variety of arrangements are possible. In particular examples, the data collection devices also include a condition evaluation subsystem that provides auto triggers, alerts and status monitoring and visualization components that continuously monitor the status of the subject, data being collected, and the data collection instruments. The condition evaluation subsystem may also present visual alerts and automatically trigger remedial actions.

According to various examples, the stimulus targeting system also includes a data cleanser device 121. In particular examples, the data cleanser device 121 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject) and endogenous artifacts (where the source could be neurophysiological like muscle movement, eye blinks, etc.).

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to various examples, the data cleanser device 121 is implemented using hardware, firmware, and/or software. It should be noted that although a data cleanser device 121 is shown located after a data collection device 105 and before data analyzer 181, the data cleanser device 121 like other components may have a location and functionality that varies based on system implementation. For example, some systems may not use any automated data cleanser device whatsoever while in other systems, data cleanser devices may be integrated into individual data collection devices.

A stimulus attributes repository 131 provides information on the stimulus material being presented to the multiple subjects. According to various examples, stimulus attributes include properties of the stimulus materials as well as purposes, presentation attributes, report generation attributes, etc. In particular examples, stimulus attributes include time span, channel, rating, media, type, etc. Purpose attributes include aspiration and objects of the stimulus including excitement, memory retention, associations, etc. Presentation attributes include audio, video, imagery, and message needed for enhancement or avoidance. Other attributes may or may not also be included in the stimulus attributes repository or some other repository.

The data cleanser device 121 and the stimulus attributes repository 131 pass data to the data analyzer 181. The data analyzer 181 uses a variety of mechanisms to analyze underlying data in the system to determine neuro-physiological and neuro-behavioral characteristics of stimulus material. According to various examples, the data analyzer customizes and extracts the independent neurological and neuro-physiological parameters for each individual in each modality, and blends the estimates within a modality as well as across modalities to elicit an enhanced response to the presented stimulus material. In particular examples, the data analyzer 181 aggregates the response measures across subjects in a dataset.

According to various examples, neuro-physiological and neuro-behavioral signatures are measured using time domain analyses and frequency domain analyses. Such analyses use parameters that are common across individuals as well as parameters that are unique to each individual. The analyses could also include statistical parameter extraction and fuzzy logic based attribute estimation from both the time and frequency components of the synthesized response.

In some examples, statistical parameters used in a blended effectiveness estimate include evaluations of skew, peaks, first and second moments, population distribution, as well as fuzzy estimates of attention, emotional engagement and memory retention responses.

According to various examples, the data analyzer 181 may include an intra-modality response synthesizer and a cross-modality response synthesizer. In particular examples, the intra-modality response synthesizer is configured to customize and extract the independent neuro-physiological and neuro-behavioral parameters for each individual in each modality and blend the estimates within a modality analytically to elicit an enhanced response to the presented stimuli. In particular examples, the intra-modality response synthesizer also aggregates data from different subjects in a dataset.

According to various examples, the cross-modality response synthesizer or fusion device blends different intra-modality responses, including raw signals and signals output. The combination of signals enhances the measures of effectiveness within a modality. The cross-modality response fusion device can also aggregate data from different subjects in a dataset.

According to various examples, the data analyzer 181 also includes a composite enhanced effectiveness estimator (CEEE) that combines the enhanced responses and estimates from each modality to provide a blended estimate of the effectiveness. In particular examples, blended estimates are provided for each exposure of a subject to stimulus materials. The blended estimates are evaluated over time to determine neuro-physiological and neuro-behavioral characteristics. According to various examples, numerical values are assigned to each blended estimate. The numerical values may correspond to the intensity of neuro-physiological and neuro-behavioral measurements, the significance of peaks, the change between peaks, etc. Higher numerical values may correspond to higher significance in neuro-physiological and neuro-behavioral intensity. Lower numerical values may correspond to lower significance or even insignificance neuro-physiological and neuro-behavioral activity. In other examples, multiple values are assigned to each blended estimate. In still other examples, blended estimates of neuro-physiological and neuro-behavioral significance are graphically represented to show effectiveness for different individuals or groups.

According to various examples, the data analyzer 181 provides analyzed and enhanced response data to a data communication system 183. According to various examples, the data communication system 183 provides raw and/or analyzed data and insights to the response integration system. In particular examples, the data communication system 183 may include mechanisms for the compression and encryption of data for secure storage and communication.

According to various examples, the data communication system 183 transmits data to the response integration using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures.

In particular examples, the data communication system 183 sends data to response integration system 185. According to various examples, the response integration system 185 combines analyzed and enhanced responses to the stimulus material while using information about stimulus material attributes. In particular examples, the response integration system 185 also collects and integrates user behavioral and survey responses with the analyzed and enhanced response data to more effectively determine neuro-physiological and neuro-behavioral response to stimulus materials.

According to various examples, the response integration system 185 obtains attributes such as requirements and purposes of the stimulus material presented. Some of these requirements and purposes may be obtained from a stimulus attribute repository 131. Others may be obtained from other sources. In particular examples, the requirements collected include attributes of the stimulus material including channel, media, time span, audience, demographic target. Other purposes may involve the target objectives of the stimulus material, such as memory retention of a brand name, association of a product with a particular feeling, etc. Still other attributes may include views and presentation specific attributes such as audio, video, imagery and messages needed, media for enhanced, media for avoidance, etc.

According to various examples, the response integration system 185 also includes mechanisms for the collection and storage of demographic, statistical and/or survey based responses to different entertainment, marketing, advertising and other audio/visual/tactile/olfactory material. If this information is stored externally, the response integration system 185 can include a mechanism for the push and/or pull integration of the data, such as querying, extraction, recording, modification, and/or updating.

According to various examples, the response integration system 185 integrates the requirements for the presented material, the assessed neuro-physiological and neuro-behavioral response measures, and the additional stimulus attributes such as demographic/statistical/survey based responses into a synthesized measure for the neuro-physiological and neuro-behavioral response to the stimuli for the selection of targeted stimulus material for presentation to particular individuals or groups.

The response integration system 185 can further include an adaptive learning component that refines user or group profiles and tracks variations in the neuro-physiological and neuro-behavioral response to particular stimuli or series of stimuli over time. This information can be made available for other purposes, such as use of the information for presentation attribute decision making. According to various examples, the response integration system 185 integrates analyzed responses to stimuli and uses stimuli attributes to generate information for the selection of selectively targeted additional stimulus material.

As with a variety of the components in the stimulus targeting system, the response integration system 185 and the presentation modification system 187 can be co-located with the rest of the system and the user, or could be implemented in a remote location. It could also be optionally separated into an assessment repository system that could be centralized or distributed at the provider or providers of the stimulus material. In other examples, the response integration system is housed at the facilities of a third party service provider accessible by stimulus material providers and/or users.

According to various examples, the presentation modification system 187 also includes mechanisms for modification of the presentation of stimulus materials in a manner appropriate for different presentation devices. For example, the presentation modification system 187 can include an automated channel selection device that can be controlled based on the outputs of the response integration system. In other examples, the presentation modification system 187 can include software/hardware calls into an electronic game or gaming consoles for modifying levels and choices in the game. In still other examples, the presentation modification system 187 can modify the actual images and messages displayed in entertainment materials based on data from the response integration system 185.

In particular examples, the presentation modification system 187 modifies portions of a video stream such as a billboard displayed in images in the video stream in order to customize messages or images shown on the billboard. A billboard in a video stream may default to a particular advertisement but may be modified to target a particular subject or group of subjects. Messages, audio sequences, and/or any other type of stimulus material may be modified or adjusted to selectively target stimulus material. In other examples, a product in an image can be dynamically modified to show different brand names based on neuro-physiological and neuro-behavioral responses.

Figure 2:
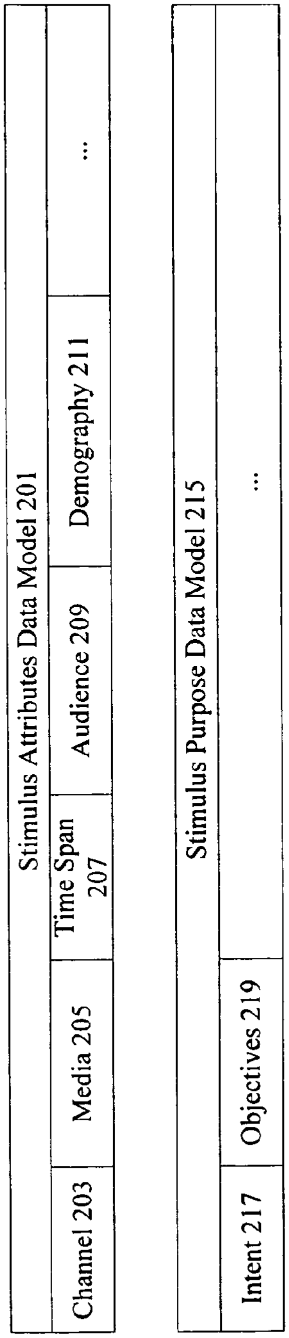
FIG. 2 illustrates examples of stimulus attributes that can be included in a stimulus attributes repository.

FIG. 2 illustrates examples of data models that may be provided with a stimulus attributes repository. According to various examples, a stimulus attributes data model 201 includes a channel 203, media type 205, time span 207, audience 209, and demographic information 211. A stimulus purpose data model 215 may include intents 217 and objectives 219.

According to various examples, intents and objectives may include memory retention of a brand name, association of a product with a particular feeling, excitement level for a particular service, etc. The attributes may be useful in providing targeted stimulus materials to multiple subjects and tracking and evaluating the effectiveness of the stimulus materials.

FIG. 3 illustrates examples of data models that can be used for storage of information associated with tracking and measurement of neuro-physiological and neuro-behavioral response. According to various examples, a dataset data model 301 includes an experiment name 303 and/or identifier, client attributes 305, a subject pool 307, logistics information 309 such as the location, date, and time of testing, and stimulus material 311 including stimulus material attributes.

In particular examples, a subject attribute data model 315 includes a subject name 317 and/or identifier, contact information 321, and demographic attributes 319 that may be useful for review of neurological and neuro-physiological data. Some examples of pertinent demographic attributes include marriage status, employment status, occupation, household income, household size and composition, ethnicity, geographic location, sex, race. Other fields that may be included in data model 315 include shopping preferences, entertainment preferences, and financial preferences. Shopping preferences include favorite stores, shopping frequency, categories shopped, favorite brands. Entertainment preferences include network/cable/satellite access capabilities, favorite shows, favorite genres, and favorite actors. Financial preferences include favorite insurance companies, preferred investment practices, banking preferences, and favorite online financial instruments. A variety of subject attributes may be included in a subject attributes data model 315 and data models may be preset or custom generated to suit particular purposes.

According to various examples, data models for neuro-feedback association 325 identify experimental protocols 327, modalities included 329 such as EEG, EOG, GSR, surveys conducted, and experiment design parameters 333 such as segments and segment attributes. Other fields may include experiment presentation scripts, segment length, segment details like stimulus material used, inter-subject variations, intra-subject variations, instructions, presentation order, survey questions used, etc. Other data models may include a data collection data model 337. According to various examples, the data collection data model 337 includes recording attributes 339 such as station and location identifiers, the data and time of recording, and operator details. In particular examples, equipment attributes 341 include an amplifier identifier and a sensor identifier.

Modalities recorded 343 may include modality specific attributes like EEG cap layout, active channels, sampling frequency, and filters used. EOG specific attributes include the number and type of sensors used, location of sensors applied, etc. Eye tracking specific attributes include the type of tracker used, data recording frequency, data being recorded, recording format, etc. According to various examples, data storage attributes 345 include file storage conventions (format, naming convention, dating convention), storage location, archival attributes, expiry attributes, etc.

A preset query data model 349 includes a query name 351 and/or identifier, an accessed data collection 353 such as data segments involved (models, databases/cubes, tables, etc.), access security attributes 355 included who has what type of access, and refresh attributes 357 such as the expiry of the query, refresh frequency, etc. Other fields such as push-pull preferences can also be included to identify an auto push reporting driver or a user driven report retrieval system.

FIG. 4 illustrates examples of queries that can be performed to obtain data associated with stimulus targeting. According to various examples, queries are defined from general or customized scripting languages and constructs, visual mechanisms, a library of preset queries, diagnostic querying including drill-down diagnostics, and eliciting what if scenarios. According to various examples, subject attributes queries 415 may be configured to obtain data from a neuro-informatics repository using a location 417 or geographic information, session information 421 such as testing times and dates, and demographic attributes 419. Demographics attributes include household income, household size and status, education level, age of kids, etc.

Other queries may retrieve stimulus material based on shopping preferences of subject participants, countenance, physiological assessment, completion status. For example, a user may query for data associated with product categories, products shopped, shops frequented, subject eye correction status, color blindness, subject state, signal strength of measured responses, alpha frequency band ringers, muscle movement assessments, segments completed, etc. Experimental design based queries may obtain data from a neuro-informatics repository based on experiment protocols 427, product category 429, surveys included 431, and stimulus provided 433. Other fields that may used include the number of protocol repetitions used, combination of protocols used, and usage configuration of surveys.

Client and industry based queries may obtain data based on the types of industries included in testing, specific categories tested, client companies involved, and brands being tested. Response assessment based queries 437 may include attention scores 439, emotion scores, 441, retention scores 443, and effectiveness scores 445. Such queries may obtain materials that elicited particular scores.

Response measure profile based queries may use mean measure thresholds, variance measures, number of peaks detected, etc. Group response queries may include group statistics like mean, variance, kurtosis, p-value, etc., group size, and outlier assessment measures. Still other queries may involve testing attributes like test location, time period, test repetition count, test station, and test operator fields. A variety of types and combinations of types of queries can be used to efficiently extract data.

Figure 5:
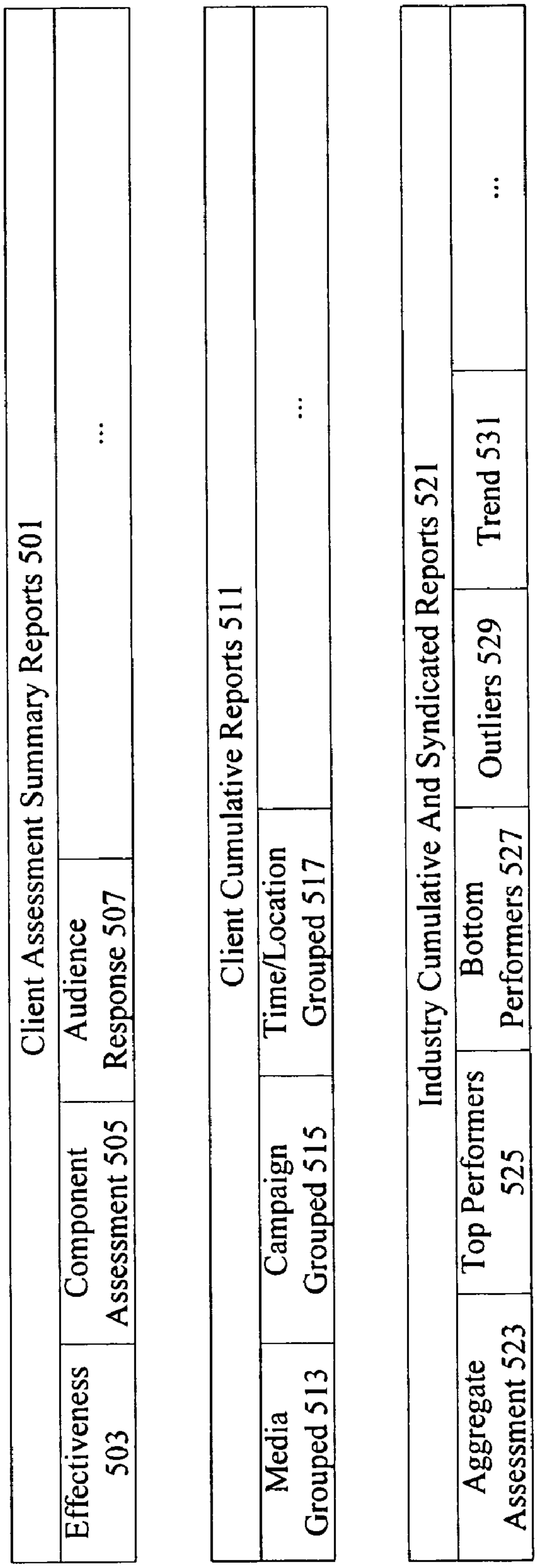
FIG. 5 illustrates one example of a report generated using the stimulus targeting system.

FIG. 5 illustrates examples of reports that can be generated. According to various examples, client assessment summary reports 501 include effectiveness measures 503, component assessment measures 505, and neuro-physiological and neuro-behavioral measures 507. Effectiveness assessment measures include composite assessment measure(s), industry/category/client specific placement (percentile, ranking, . . . ), actionable grouping assessment such as removing material, modifying segments, or fine tuning specific elements, etc, and the evolution of the effectiveness profile over time. In particular examples, component assessment reports include component assessment measures like attention, emotional engagement scores, percentile placement, ranking, etc. Component profile measures include time based evolution of the component measures and profile statistical assessments. According to various examples, reports include the number of times material is assessed, attributes of the multiple presentations used, evolution of the response assessment measures over the multiple presentations, and usage recommendations.

According to various examples, client cumulative reports 511 include media grouped reporting 513 of all stimulus assessed, campaign grouped reporting 515 of stimulus assessed, and time/location grouped reporting 517 of stimulus assessed. According to various examples, industry cumulative and syndicated reports 521 include aggregate assessment responses measures 523, top performer lists 525, bottom performer lists 527, outliers 529, and trend reporting 531. In particular examples, tracking and reporting includes specific products, categories, companies, brands.

Figure 6:
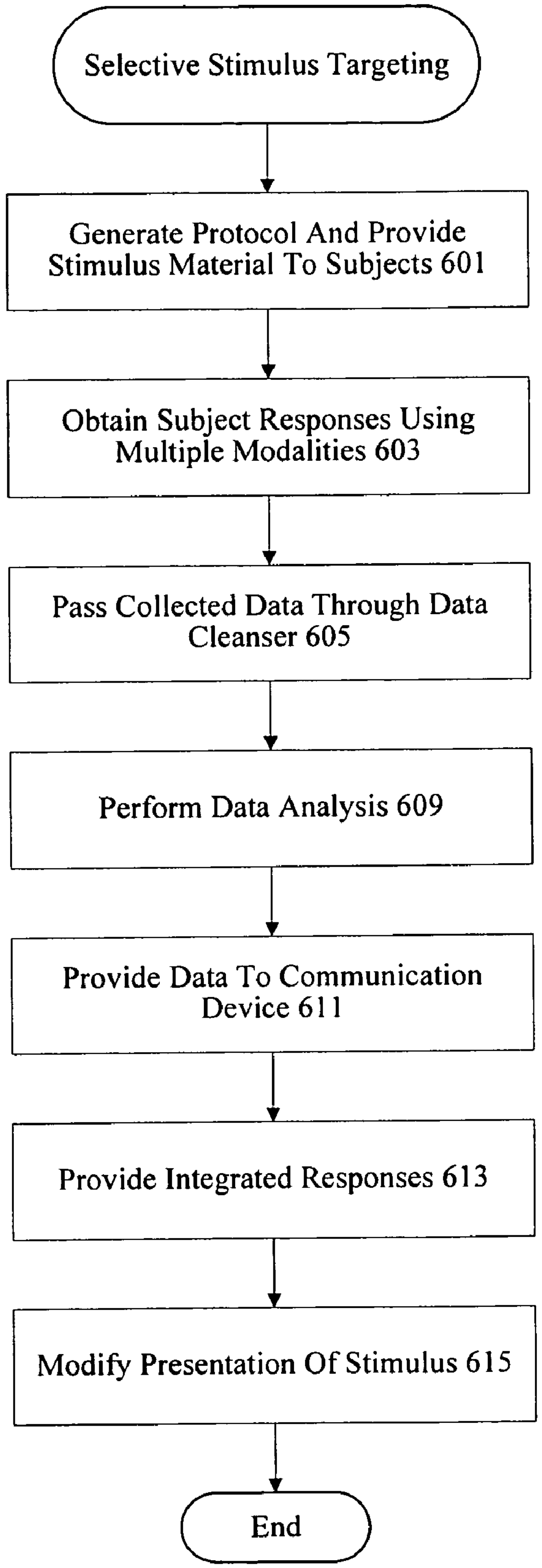
FIG. 6 illustrates one example of a technique for performing stimulus targeting.

FIG. 6 illustrates one example of stimulus targeting. At 601, a protocol is generated and stimulus material is provided to one or more subjects. According to various examples, stimulus includes streaming video, media clips, printed materials, presentations, performances, games, etc. The protocol determines the parameters surrounding the presentation of stimulus, such as the number of times shown, the duration of the exposure, sequence of exposure, segments of the stimulus to be shown, etc. Subjects may be isolated during exposure or may be presented materials in a group environment with or without supervision. At 603, subject responses are collected using a variety of modalities, such as EEG, ERP, EOG, GSR, etc. In some examples, verbal and written responses can also be collected and correlated with neurological and neurophysiological responses. At 605, data is passed through a data cleanser to remove noise and artifacts that may make data more difficult to interpret. According to various examples, the data cleanser removes EEG electrical activity associated with blinking and other endogenous/exogenous artifacts.

At 609, data analysis is performed. Data analysis may include intra-modality response synthesis and cross-modality response synthesis to enhance effectiveness measures. It should be noted that in some particular instances, one type of synthesis may be performed without performing other types of synthesis. For example, cross-modality response synthesis may be performed with or without intra-modality synthesis.

A variety of mechanisms can be used to perform data analysis 609. In particular examples, a stimulus attributes repository 131 is accessed to obtain attributes and characteristics of the stimulus materials, along with purposes, intents, objectives, etc. In particular examples, EEG response data is synthesized to provide an enhanced assessment of effectiveness. According to various examples, EEG measures electrical activity resulting from thousands of simultaneous neural processes associated with different portions of the brain. EEG data can be classified in various bands. According to various examples, brainwave frequencies include delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved in binding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, the techniques and mechanisms of the present disclosure recognize that analyzing high gamma band (kappa-band: Above 60 Hz) measurements, in addition to theta, alpha, beta, and low gamma band measurements, enhances neurological attention, emotional engagement and retention component estimates. In particular examples, EEG measurements including difficult to detect high gamma or kappa band measurements are obtained, enhanced, and evaluated. Subject and task specific signature sub-bands in the theta, alpha, beta, gamma and kappa bands are identified to provide enhanced response estimates. According to various examples, high gamma waves (kappa-band) above 80 Hz (typically detectable with sub-cranial EEG and/or magnetoencephalography) can be used in inverse model-based enhancement of the frequency responses to the stimuli.

Various examples of the present disclosure recognize that particular sub-bands within each frequency range have particular prominence during certain activities. A subset of the frequencies in a particular band is referred to herein as a sub-band. For example, a sub-band may include the 40-45 Hz range within the gamma band. In particular examples, multiple sub-bands within the different bands are selected while remaining frequencies are band pass filtered. In particular examples, multiple sub-band responses may be enhanced, while the remaining frequency responses may be attenuated.

An information theory based band-weighting model is used for adaptive extraction of selective dataset specific, subject specific, task specific bands to enhance the effectiveness measure. Adaptive extraction may be performed using fuzzy scaling. Stimuli can be presented and enhanced measurements determined multiple times to determine the variation profiles across multiple presentations. Determining various profiles provides an enhanced assessment of the primary responses as well as the longevity (wear-out) of the marketing and entertainment stimuli. The synchronous response of multiple individuals to stimuli presented in concert is measured to determine an enhanced across subject synchrony measure of effectiveness. According to various examples, the synchronous response may be determined for multiple subjects residing in separate locations or for multiple subjects residing in the same location.

Although a variety of synthesis mechanisms are described, it should be recognized that any number of mechanisms can be applied—in sequence or in parallel with or without interaction between the mechanisms.

Although intra-modality synthesis mechanisms provide enhanced significance data, additional cross-modality synthesis mechanisms can also be applied. A variety of mechanisms such as EEG, Eye Tracking, GSR, EOG, and facial emotion encoding are connected to a cross-modality synthesis mechanism. Other mechanisms as well as variations and enhancements on existing mechanisms may also be included. According to various examples, data from a specific modality can be enhanced using data from one or more other modalities. In particular examples, EEG typically makes frequency measurements in different bands like alpha, beta and gamma to provide estimates of significance. However, the techniques of the present disclosure recognize that significance measures can be enhanced further using information from other modalities.

For example, facial emotion encoding measures can be used to enhance the valence of the EEG emotional engagement measure. EOG and eye tracking saccadic measures of object entities can be used to enhance the EEG estimates of significance including but not limited to attention, emotional engagement, and memory retention. According to various examples, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to various examples, time corrected GSR measures are used to scale and enhance the EEG estimates of significance including attention, emotional engagement and memory retention measures.

Evidence of the occurrence or non-occurrence of specific time domain difference event-related potential components (like the DERP) in specific regions correlates with subject responsiveness to specific stimulus. According to various examples, ERP measures are enhanced using EEG time-frequency measures (ERPSP) in response to the presentation of the marketing and entertainment stimuli. Specific portions are extracted and isolated to identify ERP, DERP and ERPSP analyses to perform. In particular examples, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to various examples, EOG and eye tracking is enhanced by measuring the presence of lambda waves (a neurophysiological index of saccade effectiveness) in the ongoing EEG in the occipital and extra striate regions, triggered by the slope of saccade-onset to estimate the significance of the EOG and eye tracking measures. In particular examples, specific EEG signatures of activity such as slow potential shifts and measures of coherence in time-frequency responses at the Frontal Eye Field (FEF) regions that preceded saccade-onset are measured to enhance the effectiveness of the saccadic activity data.

GSR typically measures the change in general arousal in response to stimulus presented. According to various examples, GSR is enhanced by correlating EEG/ERP responses and the GSR measurement to get an enhanced estimate of subject engagement. The GSR latency baselines are used in constructing a time-corrected GSR response to the stimulus. The time-corrected GSR response is co-factored with the EEG measures to enhance GSR significance measures.

According to various examples, facial emotion encoding uses templates generated by measuring facial muscle positions and movements of individuals expressing various emotions prior to the testing session. These individual specific facial emotion encoding templates are matched with the individual responses to identify subject emotional response. In particular examples, these facial emotion encoding measurements are enhanced by evaluating inter-hemispherical asymmetries in EEG responses in specific frequency bands and measuring frequency band interactions. The techniques of the present disclosure recognize that not only are particular frequency bands significant in EEG responses, but particular frequency bands used for communication between particular areas of the brain are significant. Consequently, these EEG responses enhance the EMG, graphic and video based facial emotion identification.

At 611, processed data is provided to a data communication device. Integrated responses are generated at 613. According to various examples, the data communication system data to the response integration using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures.

In particular examples, the data communication system sends data to the response integration system. According to various examples, the response integration system combines analyzed and enhanced responses to the stimulus material while using information about stimulus material attributes. In particular examples, the response integration system also collects and integrates user behavioral and survey responses with the analyzed and enhanced response data to more effectively measure and track neuro-physiological and neuro-behavioral response to stimulus materials. According to various examples, the response integration system obtains attributes such as requirements and purposes of the stimulus material presented.

Some of these requirements and purposes may be obtained from a variety of databases. According to various examples, the response integration system also includes mechanisms for the collection and storage of demographic, statistical and/or survey based responses to different entertainment, marketing, advertising and other audio/visual/tactile/olfactory material. If this information is stored externally, the response integration system can include a mechanism for the push and/or pull integration of the data, such as querying, extraction, recording, modification, and/or updating.

The response integration system can further include an adaptive learning component that refines user or group profiles and tracks variations in the neuro-physiological and neuro-behavioral response to particular stimuli or series of stimuli over time. This information can be made available for other purposes, such as use of the information for presentation attribute decision making. According to various examples, the response integration system builds and uses responses of users having similar profiles and demographics to provide integrated responses at 613. At 615, presentation of stimulus is modified to allow selective targeting of stimulus materials. According to various examples, additional stimulus materials for presentation to a particular subject or group of subjects are automatically selected based on integrated responses. In particular examples, a channel is automatically changed.

According to various examples, the targeted stimulus material is selected to elicit an as effective or more effective integrated response from the subject than the stimulus material originally presented to the subject. According to various examples, additional stimulus material is selected based on attribute similarities with the original stimulus material. In particular examples, various neurological and neurophysiological measurements and combinations including attention, emotion, and memory retention are used to determine the significance of neuro-physiological and neuro-behavioral responses.

Figure 7:
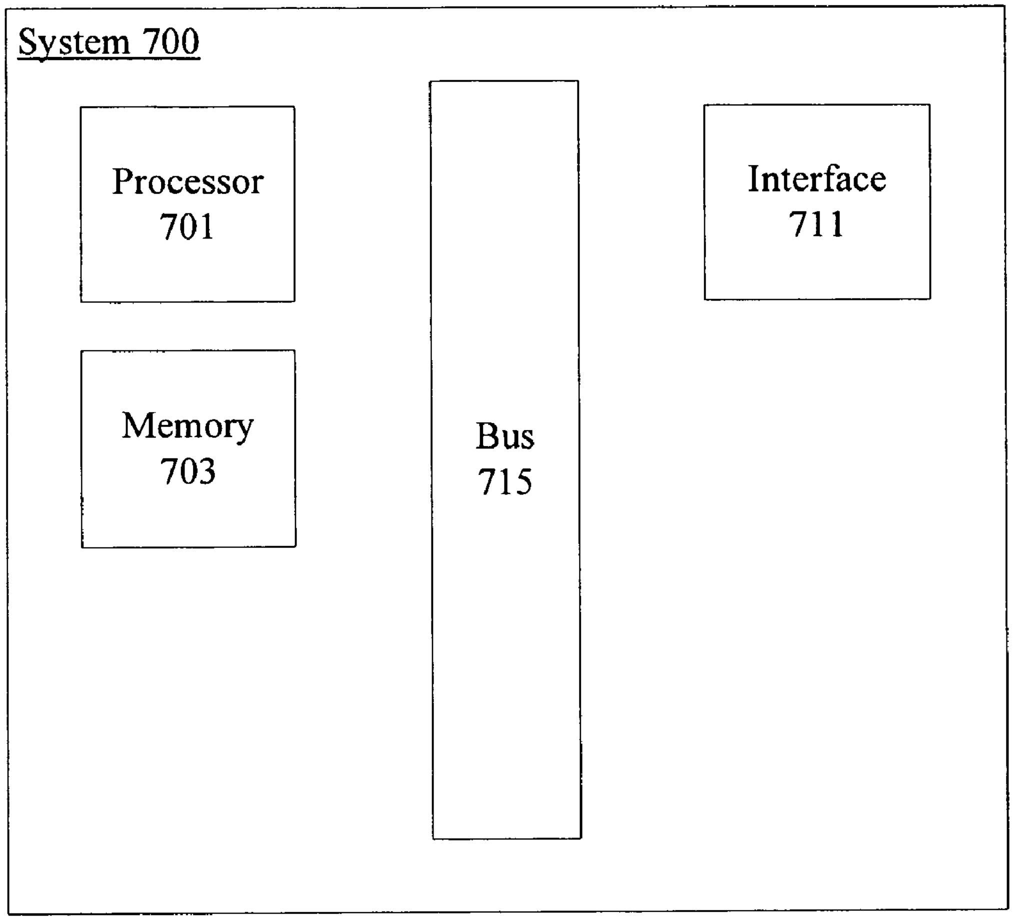
FIG. 7 provides one example of a system that can be used to implement one or more mechanisms.

According to various examples, various mechanisms such as the data collection mechanisms, the intra-modality synthesis mechanisms, cross-modality synthesis mechanisms, etc. are implemented on multiple devices. However, it is also possible that the various mechanisms be implemented in hardware, firmware, and/or software in a single system. FIG. 7 provides one example of a system that can be used to implement one or more mechanisms. For example, the system shown in FIG. 7 may be used to implement a data analyzer.

According to particular examples, a system 700 suitable for implementing particular examples of the present disclosure includes a processor 701, a memory 703, an interface 711, and a bus 715 (e.g., a PCI bus). When acting under the control of appropriate software or firmware, the processor 701 is responsible for such tasks such as pattern generation. Various specially configured devices can also be used in place of a processor 701 or in addition to processor 701. The complete implementation can also be done in custom hardware. The interface 711 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as data synthesis.

According to particular examples, the system 700 uses memory 703 to store data, algorithms and program instructions. The program instructions may control the operation of an operating system and/or one or more applications, for example. The memory or memories may also be configured to store received data and process received data.

Because such information and program instructions may be employed to implement the systems/methods described herein, the present disclosure relates to tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing disclosure has been described in some detail for purposes of clarity of understanding, it will be apparent that certain changes and modifications may be practiced within the scope of the appended claims. Therefore, the present examples are to be considered as illustrative and not restrictive and the disclosure is not to be limited to the details given herein, but may be modified within the scope and equivalents of the appended claims.

What is claimed is:

1. A system comprising:
an analyzer to:
determine a first distance between (1) a first peak in a first frequency band of first neuro-response data gathered from a subject while exposed to media and (2) a second peak in the first frequency band;
determine a second distance between (1) a third peak in the first frequency band and either (2) the second peak in the first frequency band or (3) a fourth peak in the first frequency band; and
determine a first difference between the first distance and the second distance;
a selector to determine a modification for the media based on the first difference; and
a modifier to implement the modification for presentation of the media.

2. The system of claim 1, wherein the modification includes one or more of a modification to an image or text of the media.

3. The system of claim 1, wherein the modifier is to dynamically implement the modification while the subject is exposed to the media.

4. The system of claim 1, wherein the modification is based on an attribute of the subject.

5. The system of claim 1, wherein the media is first media and wherein the selector is to identify second media for presentation to the subject based on the first difference.

6. The system of claim 1, wherein
the first peak corresponds to a first numerical value indicative of a first user intensity level during exposure to the media,
the second peak corresponds to a second numerical value indicative of a second user intensity level during exposure to the media,
the third peak corresponds to a third numerical value indicative of a third user intensity level, and
the fourth peak corresponds to a fourth numerical value indicative of a fourth user intensity level, and wherein the analyzer is to:
detect a change in user intensity based on the first difference; and
assign a level of engagement to the media based on the change in user intensity.

7. The system of claim 1, wherein the analyzer is to:
determine a third distance between (1) a fifth peak in a second frequency band of the first neuro-response data and (2) a sixth peak in the second frequency band;
determine a fourth distance between (1) a seventh peak in the second frequency band and either (2) the sixth peak in the second frequency band or (3) an eighth peak in the second frequency band; and
determine a second difference between the third distance and the fourth distance; and
wherein the selector is to determine the modification based on the first difference and the second difference.

8. The system of claim 7, wherein the first peak and the fifth peak occur substantially simultaneously, the second peak and the sixth peak occur substantially simultaneously, the third peak and the seventh peak occur substantially simultaneously, and the fourth peak and the eighth peak occur substantially simultaneously.

9. The system of claim 7, wherein the first frequency band and the second frequency band are different types of frequency bands.

10. The system of claim 7, wherein the first frequency band and the second frequency band are a same type of frequency band, the first frequency band gathered from a first hemisphere of a brain of the subject and the second frequency band gathered from a second hemisphere of the brain.

11. A tangible machine readable storage device or storage disk comprising instructions that, when executed, cause a machine to at least:

determine a first distance between (1) a first peak in a first frequency band of first neuro-response data gathered from a subject while exposed to media and (2) a second peak in the first frequency band;

determine a second distance between (1) a third peak in the first frequency band and either (2) the second peak in the first frequency band or (3) a fourth peak in the first frequency band;

determine a first difference between the first distance and the second distance;

determine a modification for the media based on the first difference; and implement the modification for presentation of the media.

12. The storage device or storage disk of claim 11, wherein the modification includes one or more of a modification to an image or text of the media.

13. The storage device or storage disk of claim 11, wherein the modification is based on an attribute of the subject.

14. The storage device or storage disk of claim 11, wherein the media is first media and wherein the instructions, when executed, further cause the machine to identify second media for presentation to the subject based on the first difference.

15. The storage device or storage disk of claim 11, wherein the instructions, when executed, further cause the machine to:

determine a third distance between (1) a fifth peak in a second frequency band of the first neuro-response data and (2) a sixth peak in the second frequency band;

determine a fourth distance between (1) a seventh peak in the second frequency band and either (2) the sixth peak in the second frequency band or (3) an eighth peak in the second frequency band;

determine a second difference between the third distance and the fourth distance; and determine the modification based on the first difference and the second difference.

16. An apparatus comprising:

memory; and processor circuitry to execute the instructions to:

determine a first distance between (1) a first peak in a first frequency band of first neuro-response data gathered from a subject while exposed to media and (2) a second peak in the first frequency band;

determine a second distance between (1) a third peak in the first frequency band and either (2) the second peak in the first frequency band or (3) a fourth peak in the first frequency band;

determine a first difference between the first distance and the second distance;

determine a modification for the media based on the first difference and an attribute of the subject; and implement the modification for presentation of the media.

17. The apparatus of claim 16, wherein the modification includes one or more of a modification to an image or text of the media.

18. The apparatus of claim 17, wherein the processor circuitry is to execute instructions to implement the modification dynamically while the subject is exposed to the media.

19. The apparatus of claim 16, wherein the media is first media and wherein the processor circuitry is to execute instructions to identify second media for presentation to the subject based on the first difference.

20. The apparatus of claim 16, wherein the processor circuity is to execute instructions to:

determine a third distance between (1) a fifth peak in a second frequency band of the first neuro-response data and (2) a sixth peak in the second frequency band;

determine a fourth distance between (1) a seventh peak in the second frequency band and either (2) the sixth peak in the second frequency band or (3) an eighth peak in the second frequency band;

determine a second difference between the third distance and the fourth distance; and determine the modification based on the first difference and the second difference.

* * * * *